(12) United States Patent
Robinson et al.

(10) Patent No.: US 10,514,338 B2
(45) Date of Patent: Dec. 24, 2019

(54) METAL-ANTIBODY TAGGING AND PLASMA-BASED DETECTION

(71) Applicant: Purdue Research Foundation, West Lafayette, IN (US)

(72) Inventors: Joseph Paul Robinson, West Lafayette, IN (US); Bartlomiej P. Rajwa, West Lafayette, IN (US); Valery P. Patsekin, West Lafayette, IN (US); Euiwon Bae, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 15/042,969

(22) Filed: Feb. 12, 2016

(65) Prior Publication Data
US 2016/0161415 A1   Jun. 9, 2016

Related U.S. Application Data

(63) Continuation-in-part of application No. PCT/US2015/049916, filed on Sep. 14, 2015.
(Continued)

(51) Int. Cl.
*G01N 21/71* (2006.01)
*G01N 33/569* (2006.01)
(Continued)

(52) U.S. Cl.
CPC .......... *G01N 21/718* (2013.01); *G01N 21/25* (2013.01); *G01N 33/569* (2013.01);
(Continued)

(58) Field of Classification Search
CPC ...... G01N 21/718; G01N 21/25; G01N 33/58; G01N 33/56911; G01N 33/569; G01N 21/67
See application file for complete search history.

(56) References Cited

U.S. PATENT DOCUMENTS

| 5,847,825 | A | * | 12/1998 | Alexander | ........... | G01N 21/718 |
| | | | | | | 356/318 |
| 6,753,957 | B1 | * | 6/2004 | Graft | .................... | G01N 21/718 |
| | | | | | | 356/318 |

(Continued)

FOREIGN PATENT DOCUMENTS

| WO | WO9945368 | 9/1999 |
| WO | WO2012125652 | 9/2012 |

OTHER PUBLICATIONS

Lou et al., Polymer-Based Elemental Tags for Sensitive Bioassays, Angew Chem Int Ed Engl., vol. 46, Issue 32, pp. 6111-6114. (Year: 2007).*

(Continued)

*Primary Examiner* — Melanie Brown
(74) *Attorney, Agent, or Firm* — Lee & Hayes, P.C.

(57) ABSTRACT

A target within a sample can be characterized using an energy source configured to transform a metal in the sample into a plasma and an optical spectroscopic detector configured to detect electromagnetic radiation emitted by the plasma to provide an optical-spectrum signal. A processor can determine presence of the metal in the sample using the optical-spectrum signal. The target can include a microbe or biological toxin. A recognition construct comprising a metal and a scaffold can be applied to the sample. The scaffold can bind to the target. Energy can be applied to transform at least some of the sample into a plasma. Electromagnetic radiation emitted by the plasma can be detected to provide an optical-spectrum signal of the sample. A preparation subsystem can add the recognition construct to the sample and a washing subsystem can wash unbound recognition construct out of the sample.

13 Claims, 25 Drawing Sheets

Related U.S. Application Data

(60) Provisional application No. 62/049,931, filed on Sep. 12, 2014.

(51) Int. Cl.
    *G01N 33/58* (2006.01)
    *G01N 21/25* (2006.01)

(52) U.S. Cl.
    CPC ....... *G01N 33/56911* (2013.01); *G01N 33/58* (2013.01); *G01N 2469/00* (2013.01); *G01N 2469/10* (2013.01)

(56) References Cited

U.S. PATENT DOCUMENTS

| | | | |
|---|---|---|---|
| 9,383,260 B1* | 7/2016 | Yoo | B23K 26/032 |
| 2003/0108973 A1 | 6/2003 | Gatto-Menking et al. | |
| 2004/0101917 A1 | 5/2004 | Robey et al. | |
| 2006/0183120 A1* | 8/2006 | Teh | C12Q 1/6886 435/6.11 |
| 2008/0020474 A1* | 1/2008 | Hayashizaki | G01N 33/54373 436/86 |
| 2009/0290151 A1 | 11/2009 | Agrawal et al. | |
| 2010/0050737 A1* | 3/2010 | Wolters | G01N 30/8665 73/23.22 |
| 2011/0109904 A1* | 5/2011 | Ugolin | G01N 21/6452 356/311 |
| 2011/0171636 A1* | 7/2011 | Melikechi | G01N 21/718 435/6.1 |
| 2011/0237446 A1* | 9/2011 | Treado | G06K 9/00147 506/8 |
| 2013/0210165 A1* | 8/2013 | Meltola | C07F 5/003 534/16 |
| 2014/0287953 A1* | 9/2014 | Gunther | H01J 49/0463 506/9 |
| 2015/0233837 A1* | 8/2015 | Coulon | G01N 21/718 506/12 |
| 2016/0116415 A1* | 4/2016 | Gaft | G01J 3/4412 356/318 |

OTHER PUBLICATIONS

Angelo, et al., "Multiplexed ion beam imaging of human breast tumors", Nature Medicine, Epub Mar. 2, 2014, 20 (4):436-42, pp. 1-2; fig 1.

Ashley, K., et al., "Interlaboratory Evaluatioin of Trace Element Determination in Workplace Air Filter Samples by Inductively Coupled Plasma Mass Spectrometry", Journal of Environmental Monitoring, 2012, vol. 14, 8 pages.

Diwakar, P. et al., "Laser-Induced Breakdown Spectroscopy for Analysis of Micro and Nanoparticles", Journal of Analytical Atomic Spectrometry, 2012, vol. 27, 10 pages.

The PCT Search Report and Written Opinion dated Dec. 11, 2015 for PCT application No. PCT/US15/49916, 6 pages.

Adams, et al., "The Visible Region Absorption Spectra of Rare-Earth Minerals," The American Mineralogist, Mar.-Apr. 1965, vol. 50, pp. 356-366.

Angel, et al., "Multiplexed ion beam imaging of human breast tumors", Nature Medicine, Epub Mar. 2, 2014, 20(4):436-42, pp. 1-2; Fig 1.

Bendall, et al., "Single-Cell Mass Cytometry of Differential Immune and Drug Responses Across a Human Hematopoietic Continuum," Science, May 6, 2011, vol. 332, pp. 687-696.

Benoist, et al., "Flow Cytometry, Amped Up," Science, May 6, 2011, vol. 332, pp. 677-678.

Bings, et al., "Atomic Spectroscopy: A Review," Analytical Chemistry, Jun. 15, 2010, vol. 82, No. 12, pp. 4653-4681.

Cheng, et al., "Detection of Botulinum Neurotoxin Serotypes A and B Using a Chemiluminescent Versus Electrochemiluminescent Immunoassay in Food and Serum," Journal of Agricultural and Food Chemistry, 2013, vol. 61, pp. 755-760.

Dixon, et al., "Feasibility of Detection and Identification of Individual Bioaerosols Using Laser-Induced Breakdown Spectroscopy," Analytical Chemistry, Jan. 15, 2005, vol. 77, No. 2, pp. 631-638.

Giesen, et al., "Highly Multiplexed Imaging of Tumor Tissues with Subcellular Resolution by Mass Cytometry," Nature Methods, Apr. 2014, vol. 11, No. 4, 9 pages.

He, et al., "Development and Characterization of Monoclonal Antibodies Against Shiga Toxin 2 and Their Application for Toxin Detection in Milk," Journal of Immunological Methods, 2013, vol. 389, pp. 18-28.

Hunter, et al., "Rapid Field Screening of Soils for Heavy Metals with Spark-Induced Breakdown Spectroscopy," Applied Optics, Apr. 20, 2003, vol. 42, No. 2, pp. 2102-2109.

Majonis, D., et al., "Synthesis of a Functional Metal-Chelating Polymer and Steps Towards Quantitative Mass Cytometry Bioassays," National Institue of Health—Public Access Author Manuscript, Nov. 1, 2010, 82(21), 20 pages.

Mohaidat, et al., "The Effect of Bacterial Environmental and Metabolic Stresses on a Laser-Induced Breakdown Spectroscopy (LIBS) Based Identification of *Escherichia coli* and *Streptococcus viridans*," Applied Spectroscopy, 2001, vol. 65, No. 4, pp. 386-392.

Multari, et al., "Detection of Biological Contaminants on Foods and Food Surfaces Using Laser-Induced Breakdown Spectroscopy (LIBS)," Journal of Agriculture and Food Chemistry, 2013, vol. 61, pp. 8687-8694.

Multari, et al., "Detection of Pesticides and Dioxins in Tissue Fats and Rendering Oils Using Laser-Induced Breakdown Spectroscopy (LIBS)," Journal of Agricultural and Food Chemistry, 2013, vol. 61, pp. 2348-2357.

Schmidt, et al., "Spark-Induced Breakdown Spectroscopy and Multivariate Analysis Applied to the Measurement of Total Carbon in Soil," Applied Optics, Mar. 1, 2012, vol. 51, No. 7, pp. B176-B182.

The Extended European Search Report dated Mar. 9, 2018 for European patent application No. 15840345.1, the EP national-phase application of PCT/US2015/049916, 13 pages.

Rehse, et al., "Identification and discrimination of Pseudomonas aeruginosa bacteria grown in blood and bile by laser-induced breakdown spectroscopy", Spectrochimica Acta, Part B, Atomic Spectroscopy, New York, NY, US vol. 16, No. 10, Sep. 26, 1997, pp. 1169-1176.

Kisker, "Particles—Silica-/Glas-/ Biodegradable Particles", retrieved Feb. 8, 2018, from <<https://www.kisker-biotech.com/frontoffice/product?produitId=KI0A-10-01>>, 3 pages.

University of Wisconsin—Madison, "DPTA—Virtual Museum of Molecules and Minerals", retrieved Feb. 9, 2018 from <<https://virtual-museum.sois.wisc.edu/display/dtpa/>>, 1 page.

Office Action for U.S. Appl. No. 15/510,319, dated Jun. 6, 2018, Robinson, "Metal-Antibody Tagging and Plasma-based Detection", 11 pages.

Office Action for U.S. Appl. No. 15/510,319, dated Dec. 21, 2018, Robinson et al, "Metal-Antibody tagging and Plasma-based Detection", 19 pages.

Office Action for U.S. Appl. No. 15/510,319, dated Nov. 14, 2018, Robinson et al, "Metal-Antibody Tagging and Plasma-based Detection", 19 pages.

* cited by examiner

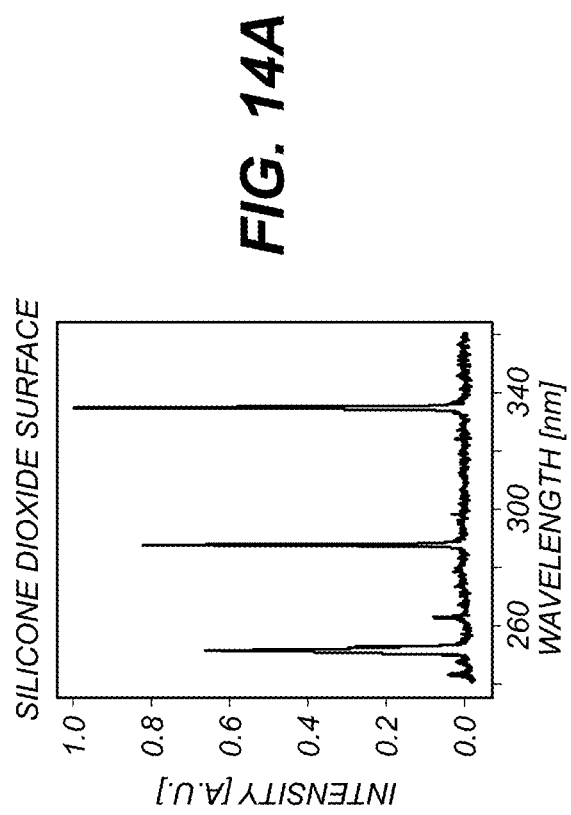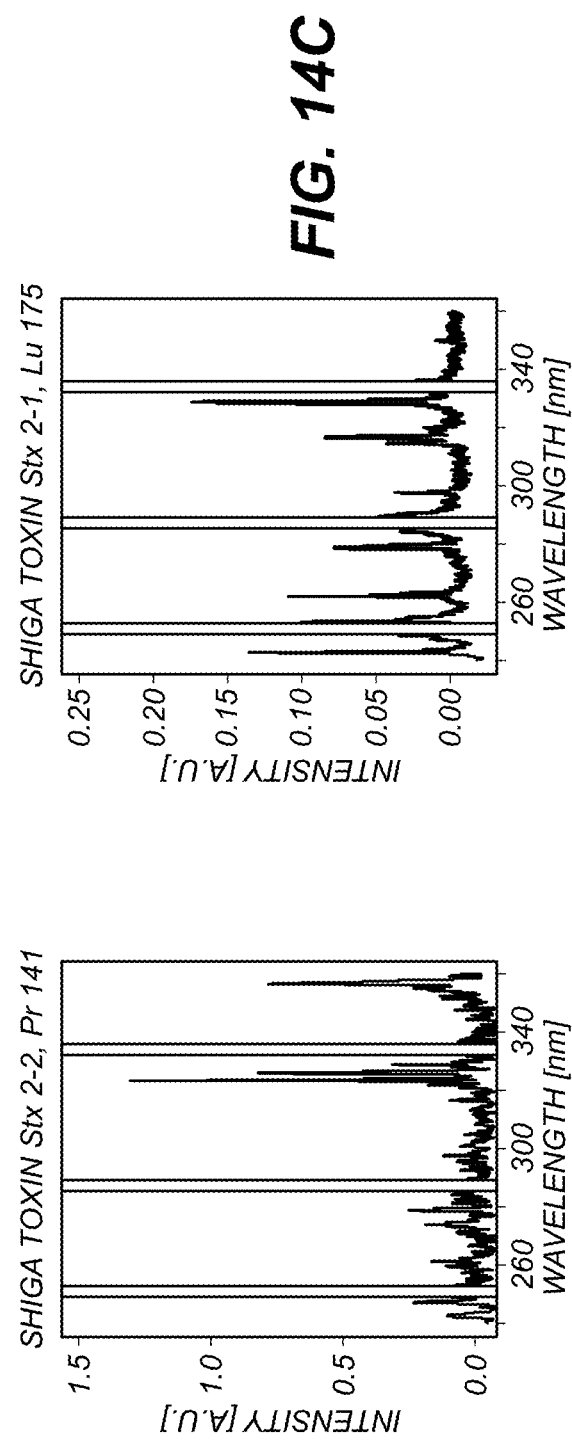

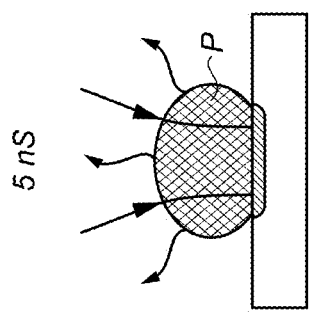 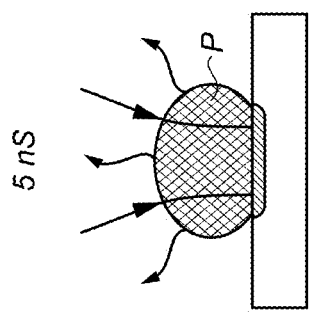 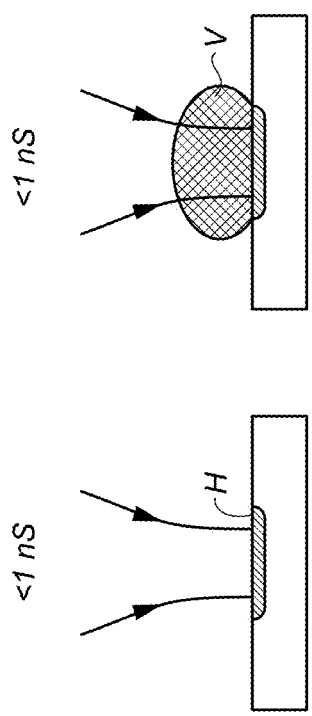 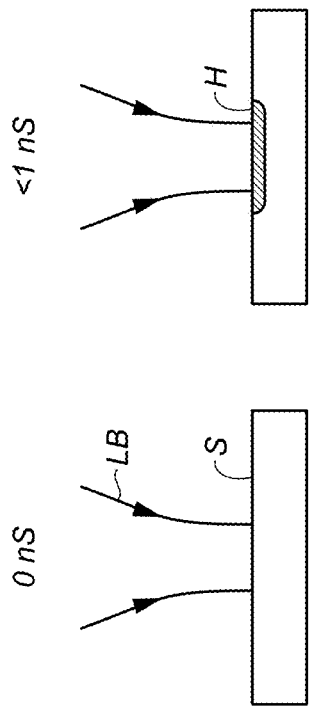
FIG. 16A  FIG. 16B  FIG. 16C  FIG. 16D
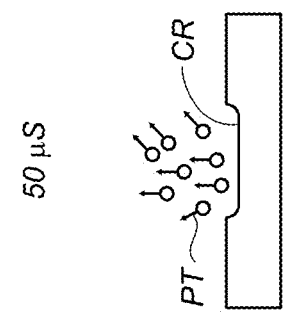 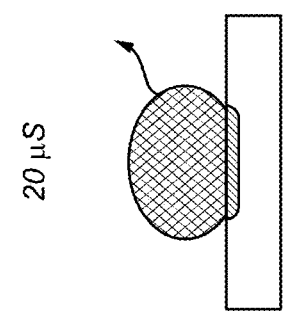 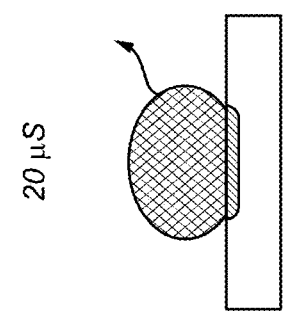 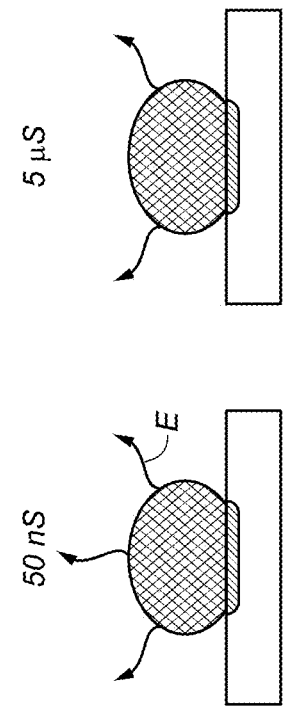
FIG. 16E  FIG. 16F  FIG. 16G  FIG. 16H

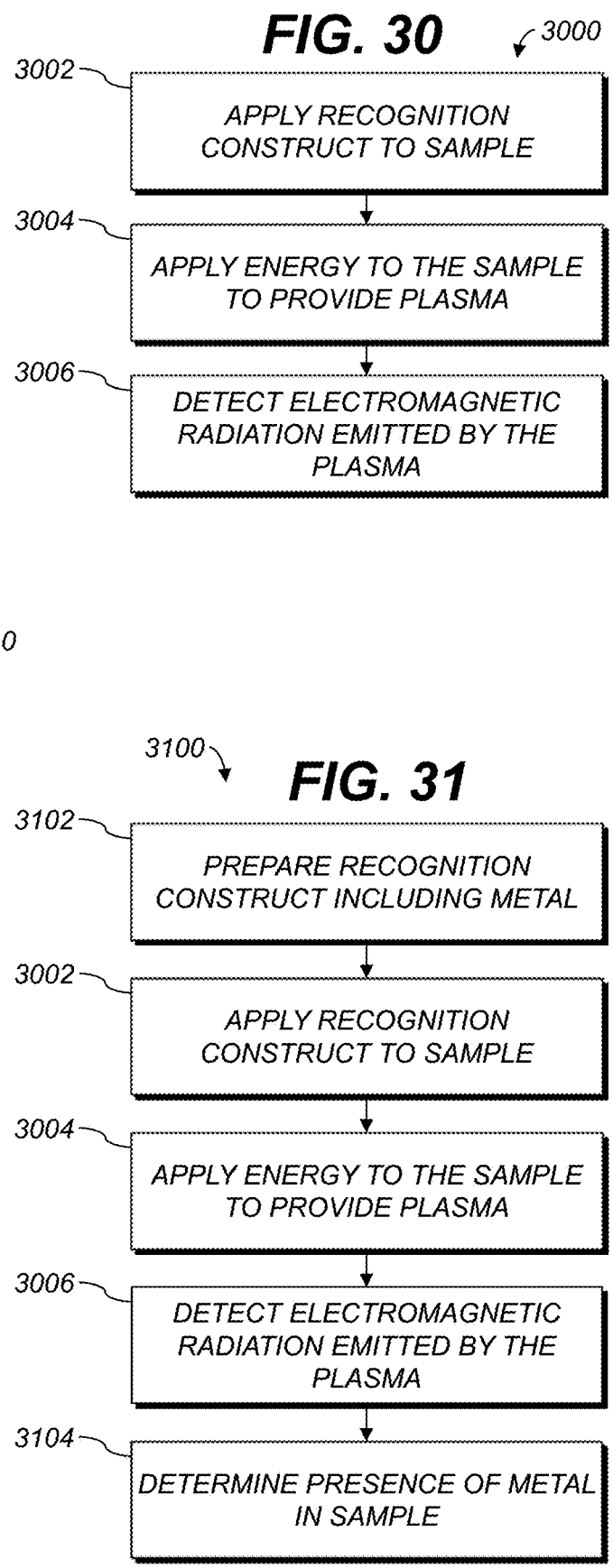
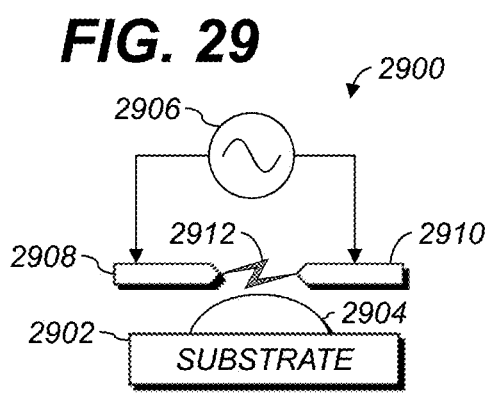

METAL-ANTIBODY TAGGING AND PLASMA-BASED DETECTION

CROSS-REFERENCE TO RELATED APPLICATIONS

The present patent application is a continuation-in-part under 35 U.S.C. 365(c) of International Application No. PCT/US2015/049916, filed Monday, Sep. 14, 2015, which is related to and claims the priority benefit of U.S. Provisional Patent Application Ser. No. 62/049,931, filed Sep. 12, 2014, the content of each of which is hereby incorporated by reference in its entirety into this disclosure.

STATEMENT OF FEDERALLY SPONSORED RESEARCH OR DEVELOPMENT

This invention was made with government support under Contract No. 59-1935-2-279 awarded by the United States Department of Agriculture. The government has certain rights in the invention.

TECHNICAL FIELD

The present disclosure generally relates to biological detection, and in particular to detection of biological pathogens using antibody tagging.

BACKGROUND

This section introduces aspects that may help facilitate a better understanding of the disclosure. Accordingly, these statements are to be read in this light and are not to be understood as admissions about what is or is not prior art.

The fields of microbiology, biosafety, and biosurveillance employ multiple detection technologies paired with various reporting modalities. The most common approaches use traditional optical labeling techniques such as fluorescence, phosphorescence, or formation of color chromophores. The optical labels are typically connected to molecular recognition molecules such as antibodies.

Other lesser-known methods for pathogen recognition or detection include detection of antibody immobilized bacteria using surface plasmon resonance (SPR) sensors, interferometric biosensors, acoustic wave biosensor platforms based on the thickness shear mode (TSM) resonator, and piezoelectric-excited millimeter-sized cantilever (PEMC) sensors. There has been also experimental work reported on detection involving microfluidic microchips coated with antibodies. The chips have an electric current passed through them. When the chip surface comes into contact with bacteria, the system shows changes in potentiometric, amperometric, or impedimetric/conductimetric characteristics demonstrating bacterial presence.

BRIEF DESCRIPTION OF THE DRAWINGS

Various objects, features, and advantages will become more apparent when taken in conjunction with the following description and drawings wherein identical reference numerals have been used, where possible, to designate features that are common to the drawings. The attached drawings are for purposes of illustration and are not necessarily to scale.

FIG. 14A is a plot of measured spectral data of a substrate.

FIG. 14B is a plot of measured spectral data of a tagged recognition construct.

FIG. 14C is a plot of measured spectral data of another tagged recognition construct.

FIGS. 16A-16H schematically illustrate an example process for analysis of a sample using SIBS.

FIG. 29 is a schematic diagram of portions of a SIBS system.

FIG. 30 is a flow diagram of an example process for analyzing a sample.

FIG. 31 is a flow diagram of an example process for analyzing a sample.

DETAILED DESCRIPTION

Overview

Figure 1:
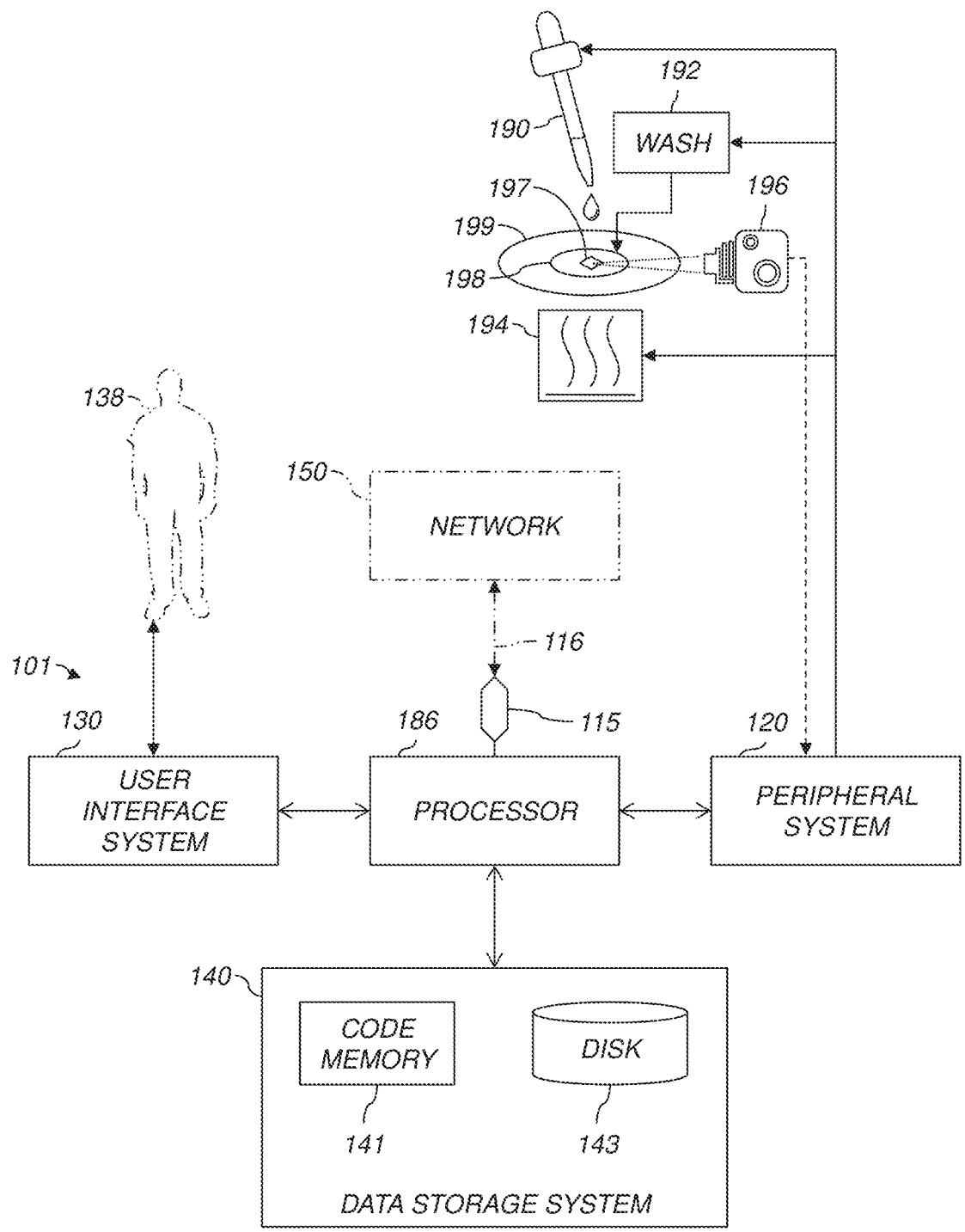
FIG. 1 is a diagram showing the components of a system for detecting a biological target in a sample.

Many prior schemes do not offer good multiplexing capability, as they are specifically designed to announce the presence of a specific type or category of bacteria. They are also not easily extendable to detect other biological hazards, such as present of biological toxins. Therefore, improvements are needed in the field. However, the claimed subject matter is not limited to implementations that solve any or all of these disadvantages or other herein-described disadvantages or limitations of prior schemes.

Various aspects herein provide optical detection of targets in samples. The target can be, e.g., biological or metallic. As used herein, the term "light" can include, but is not limited to, electromagnetic radiation in a human-visible wavelength range of, e.g., $\lambda$=400 nm-700 nm, or in a wavelength range of, e.g., 240 nm-360 nm. The term "optical" relates to structures and techniques for detecting electromagnetic radiation, e.g., in the above noted wavelength ranges or in other wavelength ranges. For example, optical detection as described herein can be used to, e.g., detect viruses on surfaces; detect pesticides or dioxins in fats or oils; analyze food-related samples for the presence of biological, biochemical, or chemical contaminants, e.g., bacteria, molds, biological toxins, pharmaceuticals, or heavy metals; detect microorganisms such as *E. coli* and *Salmonella* species; or detect toxins such as Botulinum neurotoxins (e.g., serotypes A, B, E, or F), Shiga toxins, Ricin, Abrin, mycotoxins, or bacterial toxins. Examples can include detecting Shiga or other toxins carried by bacteria, e.g., *E. coli*.

Various aspects herein provide methods and apparatus for metal-antibody tagging and plasma-based detection (MAPD), which involves the use of metal-labeled recognition macromolecules to tag infectious agents (such as bacterial cells) or toxic biological products and substances for subsequent detection using laser-induced breakdown spectroscopy (LIBS), spark induced breakdown spectroscopy (SIBS), laser ablation molecular isotopic spectrometry (LAMIS) or other detection modalities using optical spectra evaluation after plasma formation. Various herein-described detection techniques use optical emission spectroscopy. They employ a laser and a focusing lens (LIBS and LAMIS), or a spark (SIBS) to generate a plasma from the vaporized tagged sample. Various examples use microwaves or glow-discharge microwave to vaporize tagged samples to generate the plasma.

Breakdown spectroscopy as described herein allows detection of various broad classes of biological contaminants (such as microorganisms), and can serve as a sensitive detector of toxicologically important metals (e.g., light metals or heavy metals), including cadmium, arsenic, beryllium, chromium, copper, lead, mercury, thallium, nickel, and zinc. Various aspects can test for the presence of toxic organic compounds (such as polybrominated biphenyls and polybrominated diphenyl ethers), pesticides (aldrin, dieldrin, chlorpyrifos, parathion), and dioxins. Various examples do not require labeling the targets to be detected, but instead label recognition constructs as described below. Detecting targets without labeling those targets can permit detecting a wider range of compounds and more reliably attaching and detecting labels, compared to prior schemes.

In various aspects, a method for characterizing a target, e.g., a microbe or a biological toxin, includes labeling the target with a biomolecular recognition construct and measuring an optical-spectrum signal of the biomolecular recognition construct. The biomolecular recognition construct may be formed by tagging a biological or other recognition scaffold with a metal atom or ion. The target may include microbe(s), e.g., bacteria, and the biological scaffold may comprise an antibody against epitopes present on bacterial surface, the antibody linked to a heavy metal. The method can include heating the labeled target before measuring the optical-spectrum signal. The optical-spectrum signal can be measured by performing laser-induced breakdown spectroscopy (LIBS). The optical-spectrum signal can be measured by performing spark induced breakdown spectroscopy (SIBS). Data of the optical-spectrum signal can be classified using a computer-based classifier and a classification score can be assigned to the analyzed sample (e.g., spectral unmixing or spectral fingerprint classification).

Various examples incorporate at least: stable, readily-synthesizable metallic labels; a disposable solid-surface format that can be functionalized and that provides robust reference signals for calibration and data alignment; or an inexpensive readout apparatus linked to a computer-based data-processing system.

Various aspects include a transportable system able to replace a number of dedicated prior contamination detection technologies developed for single specific classes of adulterants. Various aspects process an optically-detected spectral readout using machine-learning algorithms or a database of plasma patterns to provide high-content information about a variety of tested samples. Various aspects provide a universal readout format compatible with at least three classes of contaminants (biological, organic-chemical, and inorganic-chemical).

Various aspects herein include at least an apparatus or method for characterizing a target, e.g., a microbe or a biological toxin. Apparatus can be configured to perform, or the method can include, labeling the target with a biomolecular recognition construct and measuring an optical-spectrum signal of the biomolecular recognition construct. The method can include heating the labeled target before measuring the optical-spectrum signal. The optical-spectrum signal can be measured by performing laser-induced breakdown spectroscopy. The optical-spectrum signal can be measured by performing spark induced breakdown spectroscopy. The biomolecular recognition construct can be prepared by tagging a biological scaffold with a metal atom or ion. In an aspect in which the target includes a microbial sample, the biological scaffold can include an antibody against epitopes present on bacterial surface, the antibody linked to a heavy metal. In an aspect in which the target includes a biological toxin, the biological scaffold can include an antibody against the biological toxin linked to heavy metals.

One prior scheme is dissociation-enhanced lanthanide fluorescence immunoassay (DELFIA), a fluorescence-based assay. DELFIA uses narrow-banded emission and large Stokes shift of lanthanide-diketone chelates (e.g., europium) detected via time-resolved fluorescence. However, in DELFIA, that binding between the La ions and the β-diketone ligands is too weak for the chelate-antibody conjugation.

Therefore, a multistep approach is used in which the antibody is linked with stable chelates (e.g., based on EDTA derivatives) prior to use. Subsequently the La ions are dissociated using a low-pH enhancer solution and re-chelated with β-diketone or its derivatives.

Various aspects herein, compared to DELFIA, require fewer steps of incubation, since DELFIA requires the lanthanide ions be released from the chelating polymers. The reduction in incubation provides various aspects with higher throughput than DELFIA. Various aspects can use more metals than the four lanthanides be detectable using DELFIA (europium, terbium, samarium and dysprosium). Various aspects can use five or more different metal tags in a single sample, to multiplex more than the four-way multiplexing supported by DELFIA. Various aspects provide more metal ions per antibody than the small number provided in DELFIA, due to DELFIA's low-efficiency chelation process. A higher number of ions per antibody can provide various aspects with higher signal-to-noise ratios than DELFIA. Various aspects tag monoclonal antibodies (mAbs) or other antibodies without interfering with antibody functionality, unlike the tagging process used in DELFIA, which may compromise antibody functionality.

Another prior scheme is mass cytometry, often referred to as CYTOF, in which rare-earth elements are attached to cells of interest. The cells are vaporized and any metals in those cells are detected by time-of-flight mass spectrometry. However, CYTOF requires expensive, precision equipment that may not be readily adaptable to uses in the field. In contrast, various aspects herein provide portable, inexpensive instruments that can detect metals without requiring a mass spectrometer. Various aspects herein use optical signals, e.g., intensity of plasma emission as a function of wavelength, instead of mass-spectrometer data, e.g., number of ions as a function of mass-to-charge ratio.

Illustrative Embodiments

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

FIG. 1 is a diagram showing the components of an example recognition system 101 for analyzing sample data and performing other analyses described herein, and related components. The system 101 includes a processor 186, a peripheral system 120, a user interface system 130, and a data storage system 140. The peripheral system 120, the user interface system 130, and the data storage system 140 are communicatively connected to the processor 186. Processor 186 can be communicatively connected to network 150 (shown in phantom), e.g., the Internet or a leased line, as discussed below. Lasers, sample preparation or addition devices, substrate handlers, and other devices herein can each include one or more processor(s) 186 or one or more of systems 120, 130, 140, and can each connect to one or more network(s) 150. Processor 186, and other processing devices described herein, can each include one or more microprocessors, microcontrollers, field-programmable gate arrays (FPGAs), application-specific integrated circuits (ASICs), programmable logic devices (PLDs), programmable logic arrays (PLAs), programmable array logic devices (PALs), or digital signal processors (DSPs).

Processor 186 can implement processes of various aspects described herein. Processor 186 and related components can, e.g., carry out processes for performing assays using recognition macromolecules as described in Paper 1.

Processor 186 can be or include one or more device(s) for automatically operating on data, e.g., a central processing unit (CPU), microcontroller (MCU), desktop computer, laptop computer, mainframe computer, personal digital assistant, digital camera, cellular phone, smartphone, or any other device for processing data, managing data, or handling data, whether implemented with electrical, magnetic, optical, biological components, or otherwise.

The phrase "communicatively connected" includes any type of connection, wired or wireless, for communicating data between devices or processors. These devices or processors can be located in physical proximity or not. For example, subsystems such as peripheral system 120, user interface system 130, and data storage system 140 are shown separately from the processor 186 but can be embodied or integrated completely or partially within the processor 186. In an example, processor 186 includes an ASIC including a central processing unit connected via an on-chip bus to one or more core(s) implementing function(s) of systems 120, 130, or 140.

The peripheral system 120 can include or be communicatively connected with one or more devices configured or otherwise adapted to provide digital content records to the processor 186 or to take action in response to signals or other instructions received from processor 186. For example, the peripheral system 120 can include digital still cameras, digital video cameras, spectroscopic detector 196, or other data processors. The processor 186, upon receipt of digital content records from a device in the peripheral system 120, can store such digital content records in the data storage system 140.

Processor 186 can, via peripheral system 120, control subsystems 190, 192, 194, and spectroscopic detector 196. Biological sample 198 is carried on substrate 199, which can be or include, e.g., a silicon (Si) wafer or a polystyrene (PS) sheet. Substrate 199 can be manipulated by a wafer-handling or other motion subsystem (not shown). Target 197 is shown in sample 198 for illustration. Sample 198 can include liquid, gas, powder, bulk solid, or any combination or mixture thereof. In some examples, target 197, e.g., toxin molecules or bacteria, is captured and immobilized on substrate 199 for subsequent detection as described herein.

Subsystem 190, e.g., a preparation subsystem (graphically represented as an eyedropper), is configured or otherwise adapted to add a biomolecular recognition construct to the sample 198, e.g., a dispenser or sample-deposition device such as those used in automatic dry- or wet-slide bioassays or in flow cytometry. The recognition construct can include a metal. Subsystem 192 is configured to wash at least some unbound recognition construct out of the sample 198 to provide washed sample. Subsystem 194 is configured to heat the sample-construct mixture, e.g., the sample before washing or the washed sample, so that at least some of the metal in the biomolecular recognition construct in the washed sample emits electromagnetic radiation, e.g., comprising photons at characteristic wavelength(s). This subsystem 194 can include a laser, e.g., of a type used in laser-induced breakdown spectroscopy (LIBS). Subsystem 194 can also include a spark induced breakdown spectroscopy (SIBS) spark generator, e.g., a closely-spaced electrode pair connected to a high-voltage power supply so that a high voltage can be introduced across the electrodes to produce a spark. Spectroscopic detector 196 (depicted as a camera; dashed-line connector used for clarity only) is configured to detect at least some of the electromagnetic radiation emitted by the metal, e.g., by metal atoms or ions in the recognition macromolecules. In some examples, at least some of the metal emits the electromagnetic radiation in response to the heating of the washed sample by subsystem 194, e.g., in response to energy added to the washed sample by subsystem 194.

In the illustrated example, apparatus for detecting a target 197 in a sample 198 includes subsystem 190 for adding a biomolecular recognition construct to the sample, subsystem 192 for washing unbound recognition construct out of the sample, and subsystem 194 for ionizing the sample-construct mixture into a plasma. Subsystem 194 can transform a metal in the sample into a plasma, e.g., can heat the metal until at least some of the metal vaporizes and then passes to the plasma state. The electromagnetic energy emitted by plasmas of or containing atomic and ionic species of the metals used to tag the antibodies attached to the sample can be collected by a spectrometer. The metals emit photons at characteristic wavelengths, and spectroscopic detector 196 is used for detecting photons emitted by the metal ions. The heating subsystem 194, e.g., a plasma generation subsystem, can include a laser, or can include at least two electrodes and a high-voltage power supply connected to the at least two electrodes and configured to selectively produce a spark across the at least two electrodes.

The user interface system 130 can convey information in either direction, or in both directions, between a user 138 and the processor 186 or other components of system 101. The user interface system 130 can include a mouse, a keyboard, another computer (connected, e.g., via a network or a null-modem cable), or any device or combination of devices from which data is input to the processor 186. The user interface system 130 also can include a display device, a processor-accessible memory, or any device or combination of devices to which data is output by the processor 186. The user interface system 130 and the data storage system 140 can share a processor-accessible memory.

In various aspects, processor 186 includes or is connected to communication interface 115 that is coupled via network link 116 (shown in phantom) to network 150. For example, communication interface 115 can include an integrated services digital network (ISDN) terminal adapter or a modem to communicate data via a telephone line; a network interface to communicate data via a local-area network (LAN), e.g., an Ethernet LAN, or wide-area network (WAN); or a radio to communicate data via a wireless link, e.g., WIFI or GSM (Global System for Mobile Communications). Communication interface 115 can send and receives electrical, electromagnetic, or optical signals that carry digital or analog data streams representing various types of information across network link 116 to network 150. Network link 116 can be connected to network 150 via a switch, gateway, hub, router, or other networking device.

In various aspects, system 101 can communicate, e.g., via network 150, with other data processing system(s) (not shown), which can include the same types of components as system 101 but is not required to be identical thereto. System 101 and other systems not shown can be communicatively connected via the network 150. System 101 and other systems not shown can execute computer program instructions to measure constituents of samples or exchange spectra or other data, e.g., as described herein.

Processor 186 can send messages and receive data, including program code, through network 150, network link 116, and communication interface 115. For example, a server can store requested code for an application program (e.g., a JAVA applet) on a tangible non-volatile computer-readable storage medium to which it is connected. The server can retrieve the code from the medium and transmit it through network 150 to communication interface 115. The received code can be executed by processor 186 as it is received, or stored in data storage system 140 for later execution.

Data storage system 140 can include or be communicatively connected with one or more processor-accessible memories configured or otherwise adapted to store information. The memories can be, e.g., within a chassis or as parts of a distributed system. The phrase "processor-accessible memory" is intended to include any data storage device to or from which processor 186 can transfer data (e.g., using components of peripheral system 120). A processor-accessible memory can include one or more data storage device(s) that are volatile or nonvolatile, that are removable or fixed, or that are electronic, magnetic, optical, chemical, mechanical, or otherwise. Example processor-accessible memories include but are not limited to: registers, floppy disks, hard disks, tapes, bar codes, Compact Discs, DVDs, read-only memories (ROM), erasable programmable read-only memories (EPROM, EEPROM, or Flash), and random-access memories (RAMs). One of the processor-accessible memories in the data storage system 140 can be a tangible non-transitory computer-readable storage medium, i.e., a non-transitory device or article of manufacture that participates in storing instructions that can be provided to processor 186 for execution.

In an example, data storage system 140 includes code memory 141, e.g., a RAM, and disk 143, e.g., a tangible computer-readable rotational storage device or medium such as a hard drive. In this example, computer program instructions are read into code memory 141 from disk 143. Processor 186 then executes one or more sequences of the computer program instructions loaded into code memory 141, as a result performing process steps described herein. In this way, processor 186 carries out a computer implemented process. For example, steps of methods described herein, blocks of block diagrams herein, and combinations of those, can be implemented by computer program instructions. Code memory 141 can also store data.

Various aspects described herein may be embodied as systems or methods. Accordingly, various aspects herein may take the form of an entirely hardware aspect, an entirely software aspect (including firmware, resident software, micro-code, etc.), or an aspect combining software and hardware aspects These aspects can all generally be referred to herein as a "service," "circuit," "circuitry," "module," or "system."

Furthermore, various aspects herein may be embodied as computer program products including computer readable program code ("program code") stored on a computer readable medium, e.g., a tangible non-transitory computer storage medium or a communication medium. A computer storage medium can include tangible storage units such as volatile memory, nonvolatile memory, or other persistent or auxiliary computer storage media, removable and non-removable computer storage media implemented in any method or technology for storage of information such as computer-readable instructions, data structures, program modules, or other data. A computer storage medium can be manufactured as is conventional for such articles, e.g., by pressing a CD-ROM or electronically writing data into a Flash memory. In contrast to computer storage media, communication media may embody computer-readable instructions, data structures, program modules, or other data in a modulated data signal, such as a carrier wave or other transmission mechanism. As defined herein, "computer storage media" do not include communication media. That is, computer storage media do not include communications media consisting solely of a modulated data signal, a carrier wave, or a propagated signal, per se.

The program code can include computer program instructions that can be loaded into processor 186 (and possibly also other processors), and that, when loaded into processor 186, cause functions, acts, or operational steps of various aspects herein to be performed by processor 186 (or other processor). The program code for carrying out operations for various aspects described herein may be written in any combination of one or more programming language(s), and can be loaded from disk 143 into code memory 141 for execution. The program code may execute, e.g., entirely on processor 186, partly on processor 186 and partly on a remote computer connected to network 150, or entirely on the remote computer.

Using the system 101, the biomolecular recognition construct can be prepared by tagging a biological scaffold with a metal atom or ion. The biological scaffold may comprise adNectins, iMabs, anticalins, microbodies, peptide aptamers, designed ankyrin repeat proteins (DARPins), affilins, tetranectins, avimers, or other molecules configured to bind to targets. In an aspect in which the target includes a microbe such as a bacterium, the biological scaffold can include an antibody against epitopes present on the bacterial surface, said antibody linked to a heavy metal. In an aspect in which the target includes a biological toxin, the biological scaffold can include an antibody against the biological toxin linked to heavy metals.

The construct for the molecular recognition system may be tagged using various metallic elements such as Al, Ca, Cr, Cu, Fe, Mg, Mn, Pb, Si, Ti, V and Zn. However, in order to minimize the background it is advisable to use lanthanide metals (rare earth elements) which are typically not present in biological material such as La, Ce, Pr, Nd, Pm, Sm, Eu, Gd, Tb, Dy, Ho, Er, Tm, Yb, and Lu. The probes can be prepared by coupling the scaffold for molecular recognition to polymers equipped with metal-binding ligands. These polymers contain a functional group enabling them to be covalently attached to biological macromolecules such as antibodies, while simultaneously binding to one or more metals, e.g., metal atoms or ions. Various aspects use lanthanide metals (rare earth elements), which are typically not present in biological material (La, Ce, Pr, Nd, Pm, Sm, Eu, Gd, Tb, Dy, Ho, Er, Tm, Yb, and Lu). However, various aspects herein can be also employed with chelated heavy metal ions, assuming that the heavy metals used as labels in a particular test are not themselves targets to be detected in that test. For example, in tests for heavy-metal contamination of food, metals other than heavy metals can be used as tags.

Example recognition constructs described herein can be prepared by coupling the scaffold for molecular recognition to polymers equipped with metal-binding ligands (e.g., metal-chelating polymers, MCPs). These specially designed polymers contain a functional group enabling them to be covalently attached to biological macromolecules, while simultaneously binding multiple ions of metals. Various aspects include antibodies tagged via a reaction involving selective reduction of disulfide bonds in their hinge region, followed by thiol addition to a maleimide group at one end of the metal-chelating polymer (MCP). Owing to unique and distinguishable atomic spectral signals from many other metals, various aspects can also take advantage of alternative non-MCP labeling strategies, for example using HgS nanoparticles, silver nanoparticles, organic mercury compounds, or ruthenium compounds. Additionally ions derived from cadmium, mercury, cobalt, arsenic, copper, chromium and selenium can also be identified. In some examples, molybdenum, vanadium, strontium, europium, terbium, samarium, or dysprosium can be used as tags.

The prepared recognition biomolecular recognition constructs (macromolecules) are subsequently used to perform the assay. There are many possible ways for the recognition biomolecular recognition construct to be used. In one example, a biological specimen containing pathogens or toxins can be attached to an inert surface (e.g. such as a silicon wafer). A metal-tagged antibody or an alternative molecular recognition construct is applied over the surface binding to the exposed antigens. The excess antibody or other recognition macromolecule can be removed by washing the substrate In another example, in an indirect setting following the attachment of the bacteria cells or toxin macromolecules to the surface of the inert sample holder a primary antibody or other recognition macromolecule is added, binding specifically to the antigens of interest. This primary molecular recognition system is not tagged, in contrast to the reagents described above. Subsequently a secondary (metal-tagged) macromolecule is added binding to the primary macromolecule.

In a further example, an inert surface is functionalized and covered with recognition macromolecules. The biological specimen is added and the antigens of interest are captured by the surface-bound recognition macromolecules. In the last step, the metal-tagged recognition macromolecules are added binding to the immobilized antigen. At least some of the excess unbound macromolecules are removed by a wash, e.g., by subsystem 192, FIG. 1.

Following the tagging step in these and other aspects, the specimen containing the sample of interest labeled by metal-tagged recognition molecules is analyzed using system 101 by employing one of the optical-spectroscopy techniques mentioned above. In an aspect using LIBS spectroscopy, subsystem 194 focuses a laser beam onto the inert surface (e.g., the silicon wafer) where the sample 198 is deposited. Owing to the large power density of the laser the tagged material starts to evaporate leading to the generation of plasma. The chemical constituents of the biological material are excited by the laser beam and emit electromagnetic radiation (light, e.g., human-visible or otherwise) which is element specific, upon which the radiation is detected by detector 196.

In the described settings, simultaneous (multiplexed) analysis of many targets 197 within the sample 198 is possible by utilizing a cocktail of recognition macromolecules (e.g., a mixture of antibodies), each class of recognition macromolecules labeled with a different metal. Owing to distinguishability and specificity of optical spectra produced by plasmas of different metals, this tagging arrangement permits effective multiplexing, i.e., simultaneous detection of multiple targets (for instance, different bacterial pathogens or toxins).

The plasma signal emitted by atomic and ionic species of the metals used to tag the antibodies attached to the sample can be collected using a spectrometer, such as detector 196. The naturally occurring chemical constituents of the biological sample 198 can also contribute to the spectra signal. In fact, it has been disclosed and demonstrated that the LIBS signal from bacteria alone may lead to recognition of some bacterial species. However, owing to a high similarity in biochemical composition of bacterial species, the classification ability of the label-free methods is relatively low. The spectra are used to determine the elemental constituents of the sample 198, and such constituents are similar for many bacteria or other targets. In various aspects, since the metals used to label the antibodies are either not naturally present in the tested sample 198 of interest or present only in very small quantities, the detection of the spectra of those metals is a direct indicator of a sample type and origin.

Various aspects include digitization of the recorded spectra, followed by spectral unmixing (allowing for the determination of the individual spectral constituents) or spectral fingerprint classification (involving matching the obtained spectrum to other spectra present in the database).

The disclosed system 101 therefore offers faster and more sensitive detection with reduced sample processing and preparation compared to prior art schemes. The presently disclosed detection format allows for multiplexing, e.g. simultaneous detection of multiple bacterial species, biological toxins, or other targets.

Some examples implement system 101 as a bench based device, operating on a conventional laboratory power source. Various aspects permit easy access to samples. Various aspects of system 101 include a sample collection station configured to accept a disposable single-use device that will carry the sample and final assay combination. Various examples measure panels of potential antigens, e.g., a toxin panel, a *Salmonella* panel, or a panel of common water-borne pathogens According to various aspects, system 101 is configured to characterize a target 197 within a sample 198. System 101 comprises, in some examples, an energy source (e.g., subsystem 194) configured to transform a metal in the sample 198 into a plasma. An optical spectroscopic detector (e.g., detector 196) is configured to detect electromagnetic radiation emitted by the plasma to provide an optical-spectrum signal. In some examples, substrate 199 of system 101 is configured to retain the sample 198 in operative arrangement with the energy source (194) to receive energy from the energy source (194). In some examples, the substrate 199 comprises silicon or polystyrene. The substrate 199 can further comprise recognition macromolecules, e.g. capture antibodies 2302 or detection antibodies 2306, FIG. 23.

In some examples, processor 186 executes instructions stored in a processor-accessible memory (e.g., data storage system 140). The instructions cause the processor to determine presence of the metal in the sample based at least in part on the optical-spectrum signal. Examples are discussed below, e.g., with reference to step 3104, FIG. 31. In some examples, the processor 186 performs spectral unmixing or spectral fingerprint classification on the optical-spectrum signal, as discussed below.

In some examples, processor 186 determines presence of a second metal in the sample based at least in part on the optical-spectrum signal. The second metal is different from the metal. In some examples, any number of different metals can be detected in sample 198. The different metals can be incorporated in different recognition constructs to detect different targets 197 in the sample 198.

In some examples, components of system 101 constitute apparatus for detecting a biological target 197 in a sample 198. The apparatus can include a preparation subsystem (e.g., subsystem 190) configured to add a recognition construct (e.g., construct 1100, FIG. 11) to the sample 198. The recognition construct can include a metal (e.g., ions 1106, FIG. 11). A washing subsystem 192 can be configured to wash unbound recognition construct out of the sample 198. A heating subsystem 194 can be configured to heat the washed sample 198 to cause the metal in the washed sample 198 to emit photons at characteristic wavelengths. A spectroscopic detector 196 can be configured to detect at least some of the photons. In some examples, heating subsystem 194 includes a laser. Examples are discussed below, e.g., with reference to FIGS. 17A and 28. In some examples, the heating subsystem comprises two electrodes 2908, 2910 (FIG. 29) and a high-voltage power supply 2906 connected to the two electrodes 2908, 2910 and configured to selectively produce a spark 2912 across the two electrodes 2908, 2910.

Figure 2:
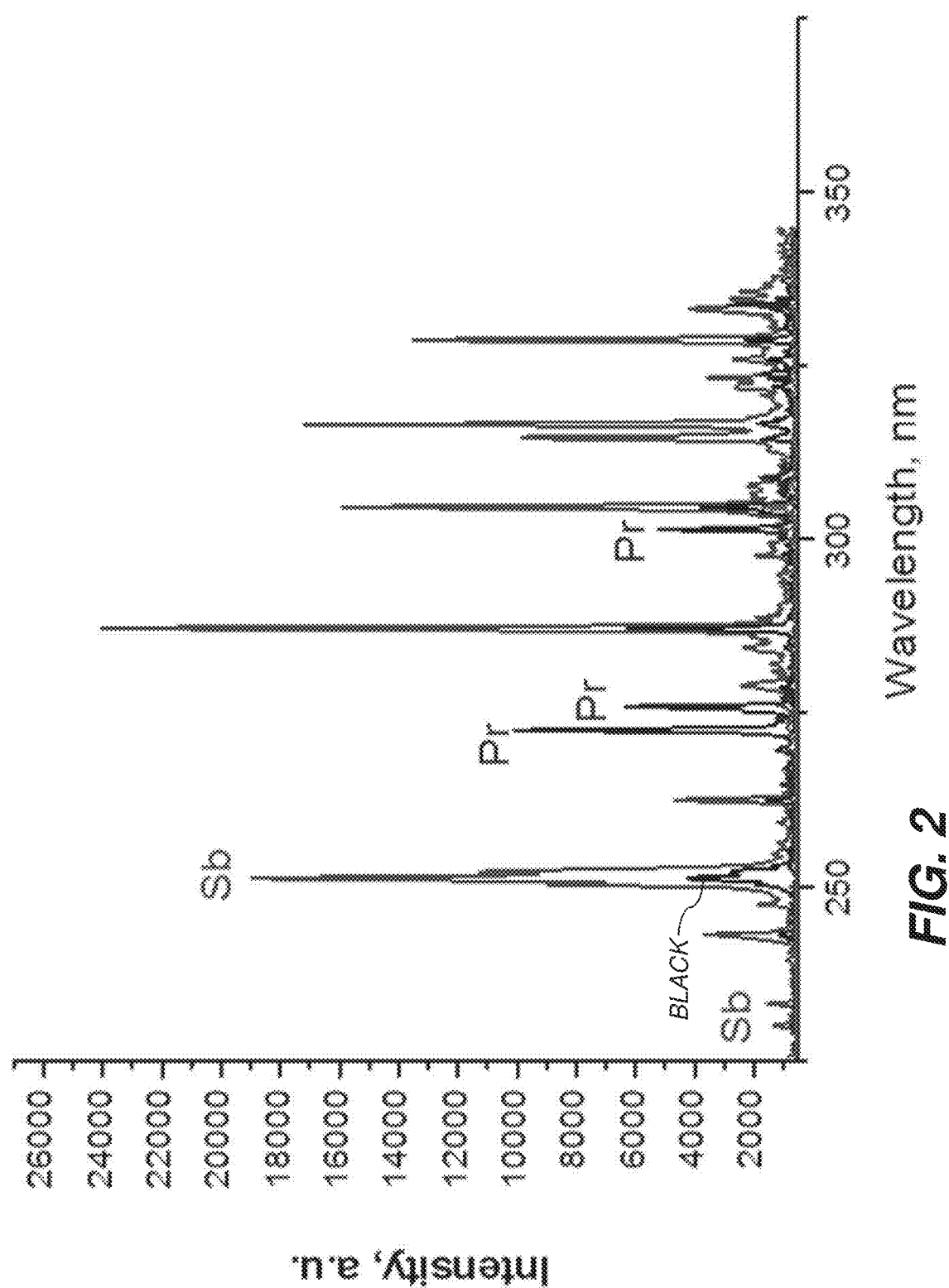
FIG. 2 is a plot showing example data that were collected in an experiment that where samples containing bacteria were labeled with two different metal-tagged antibodies, Sb and Pr according to one embodiment.

FIG. 2 shows an example plot of an experiment in which samples containing bacteria were labelled with two different types of antibodies. The Sb-tagged antibodies (indicated by Sb) attached to *E. coli* can be readily distinguished from Pr-tagged antibodies (indicated by Pr).

Figure 3:
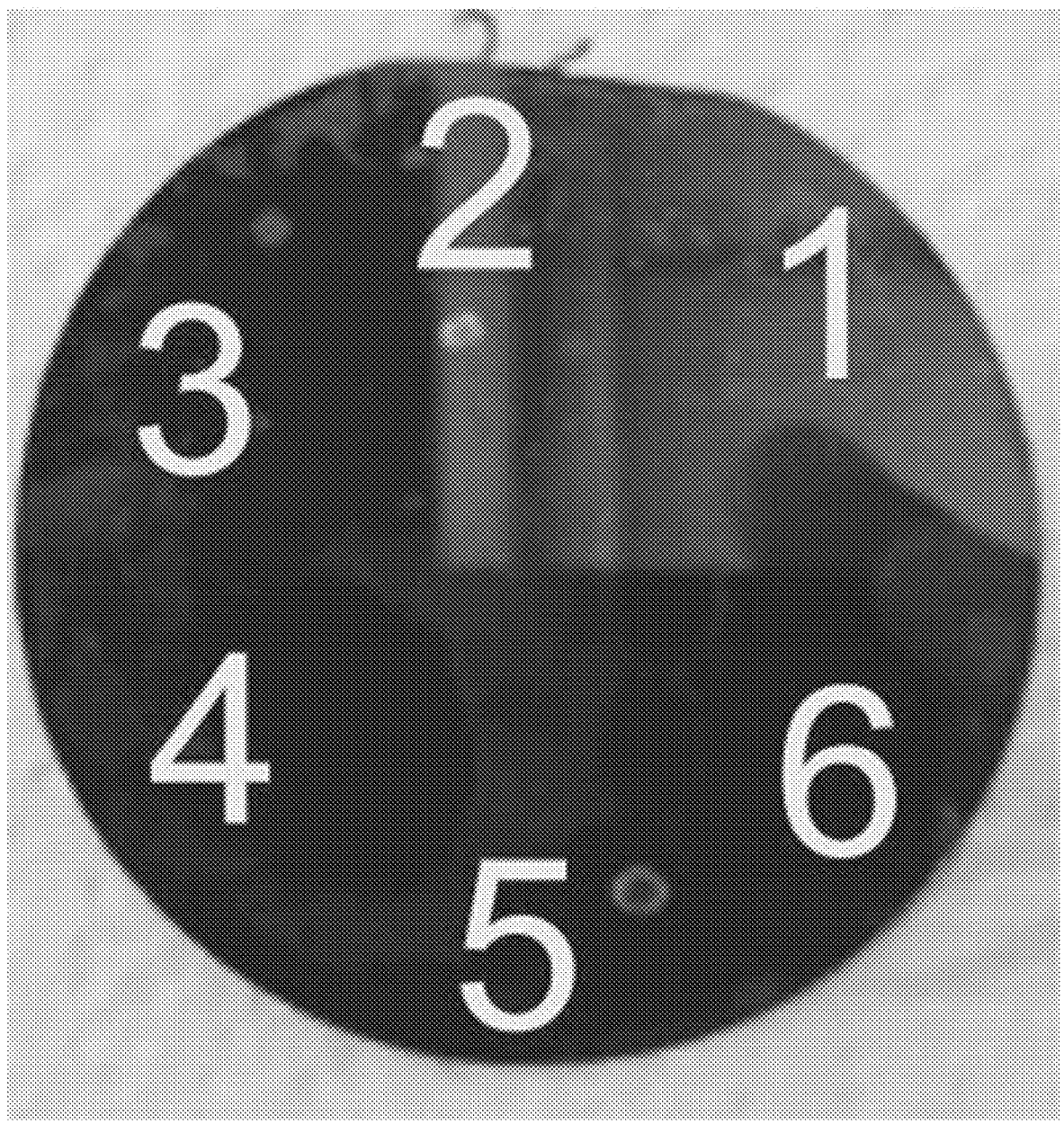
FIG. 3 is an annotated graphical representation of a photograph of an example configuration of a silicon wafer to hold sample(s).

FIG. 3 shows an example of a Silicon wafer with spotted samples (numbered 1-6) on the surface. Each spot is analyzed using the techniques described above. Results described herein were based on measurements made in this manner.

Figure 4:
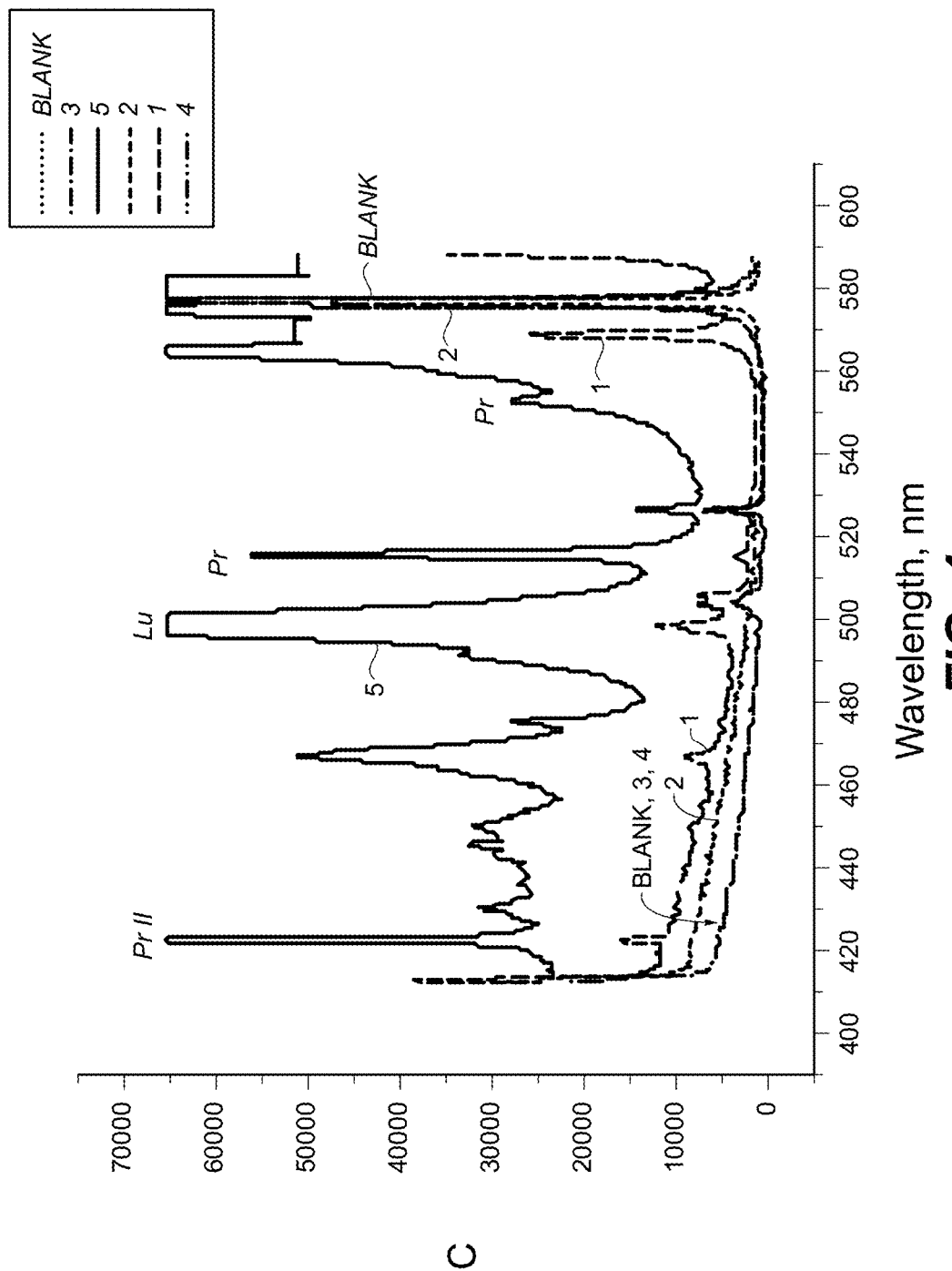
FIG. 4 is a plot showing spectral measurement of a sample containing antitoxin antibodies labeled with Lu and Pr in the 400-600 nm range according to one embodiment.

FIG. 4 is a plot showing spectral measurement of a sample containing antitoxin antibodies labeled with Lu and Pr in the 400-600 nm range.

Figure 5:
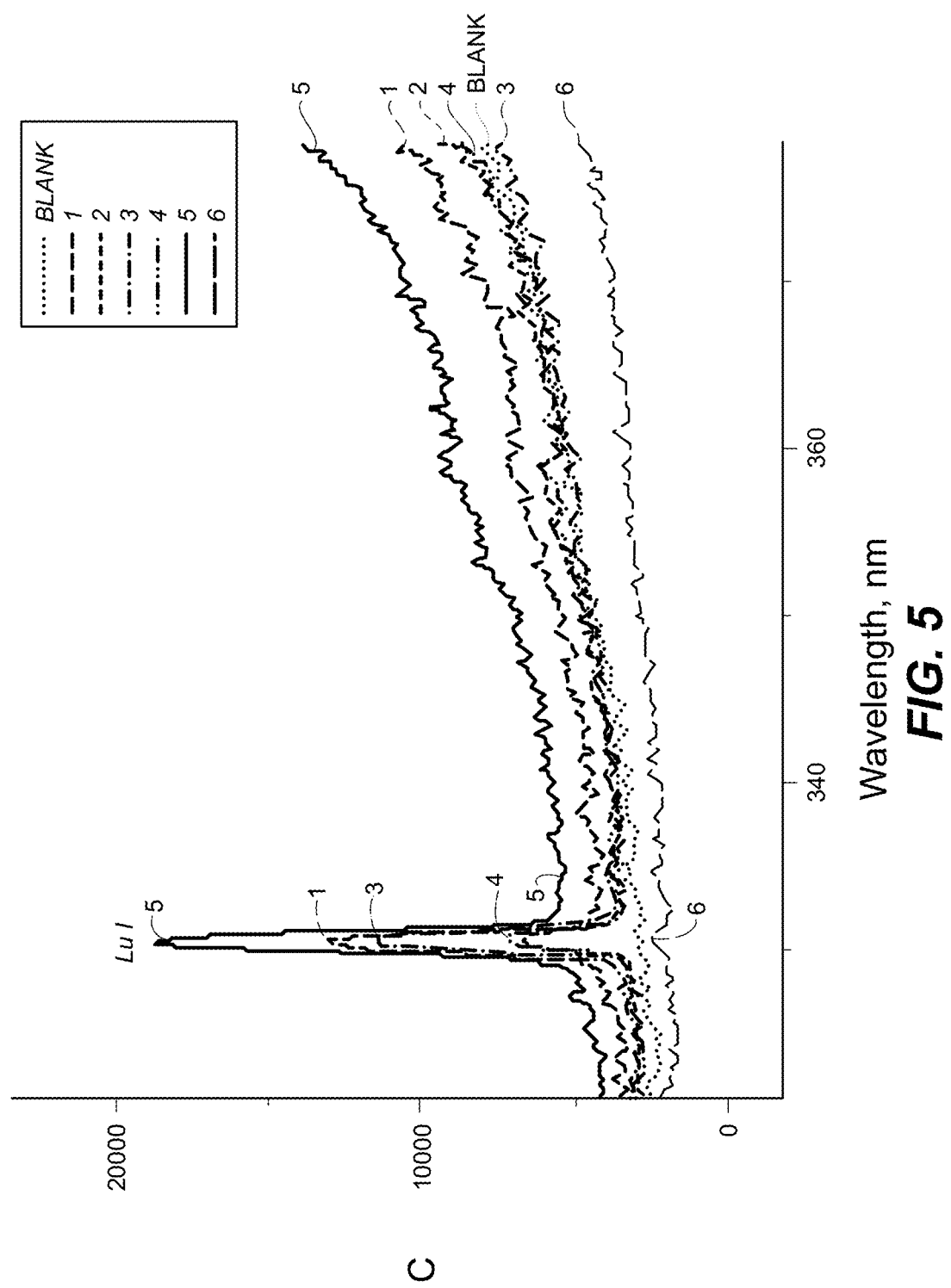
FIG. 5 is a plot showing spectral measurement of a sample containing antitoxin antibodies labeled with Lu and Pr in the 320-380 nm range according to one embodiment.

FIG. 5 is a plot showing spectral measurement of a sample containing antitoxin antibodies labeled with Lu and Pr in the 320-380 nm range.

Figure 6:
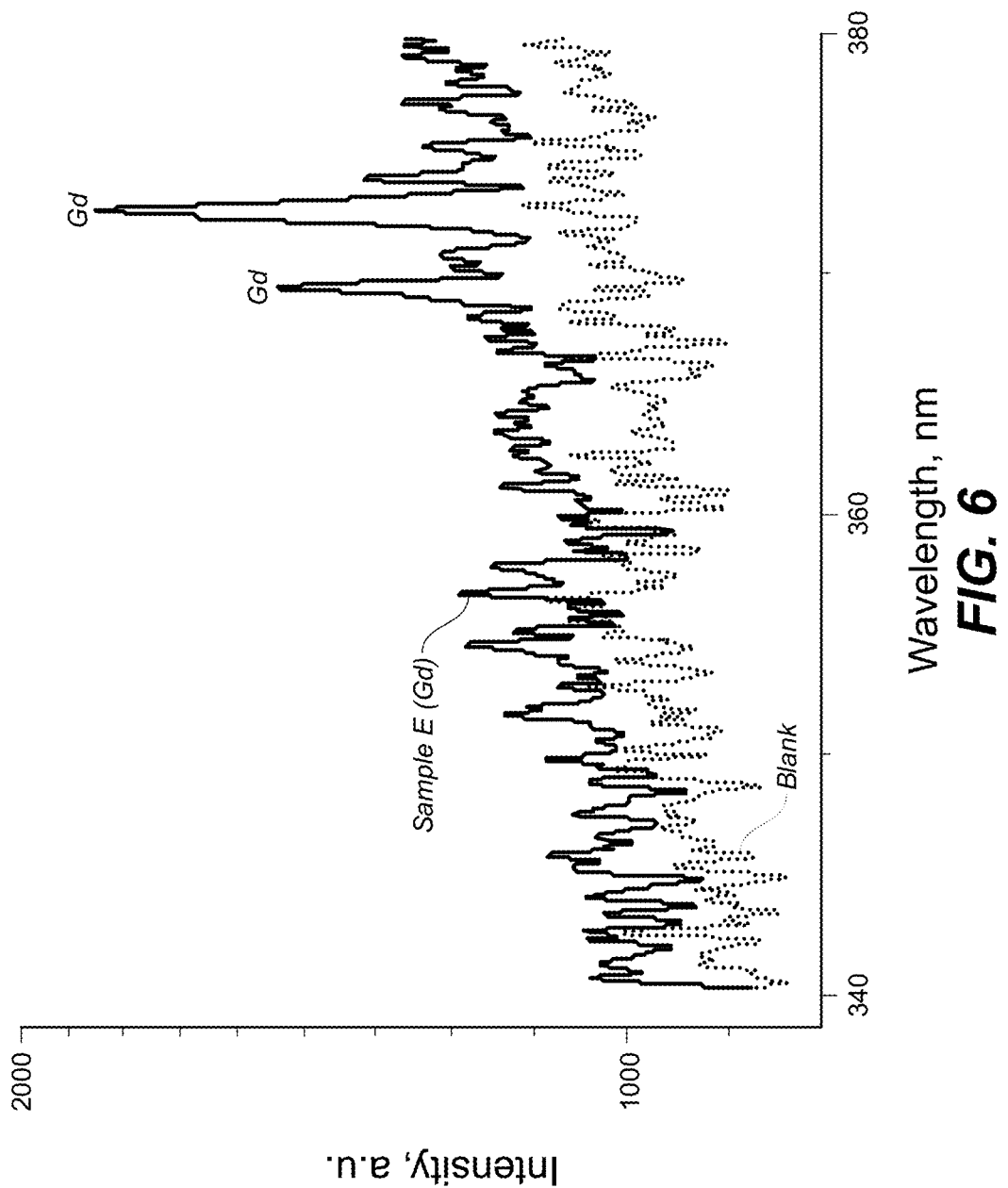
FIG. 6 is a plot showing spectral measurement of a sample containing antitoxin antibodies labeled with $^{156}$Gd and a blank sample in the 340-380 nm range according to one embodiment.

FIG. 6 is a plot showing spectral measurement of a sample containing antitoxin antibodies labeled with $^{156}$Gd and a blank sample in the 340-380 nm range.

Figure 7:
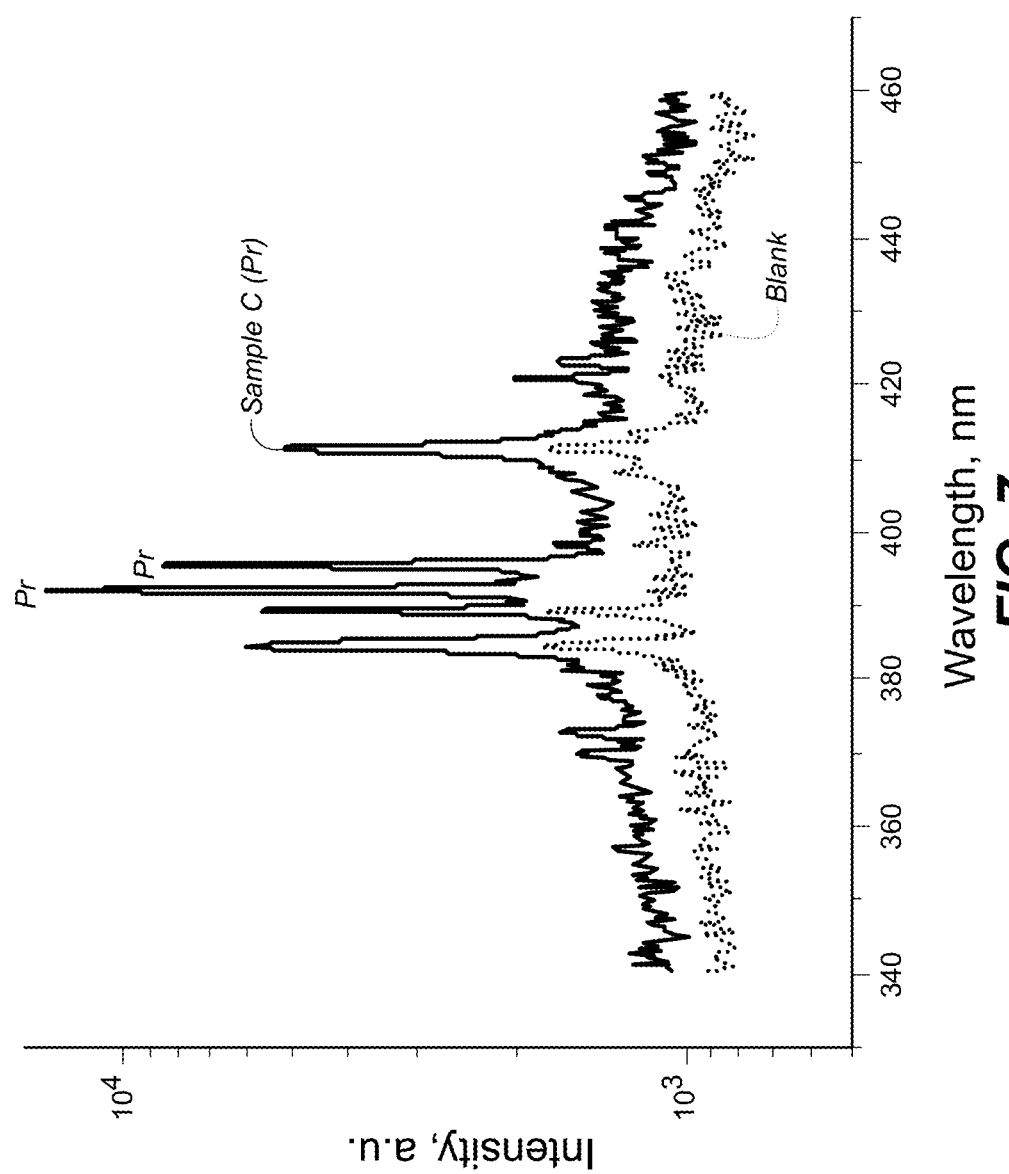
FIG. 7 is a plot showing spectral measurement of a sample containing antitoxin antibodies labeled with Pr in the 340-460 nm range according to one embodiment.

FIG. 7 is a plot showing spectral measurement of a sample containing antitoxin antibodies labeled with Pr in the 340-460 nm range.

Figure 8:
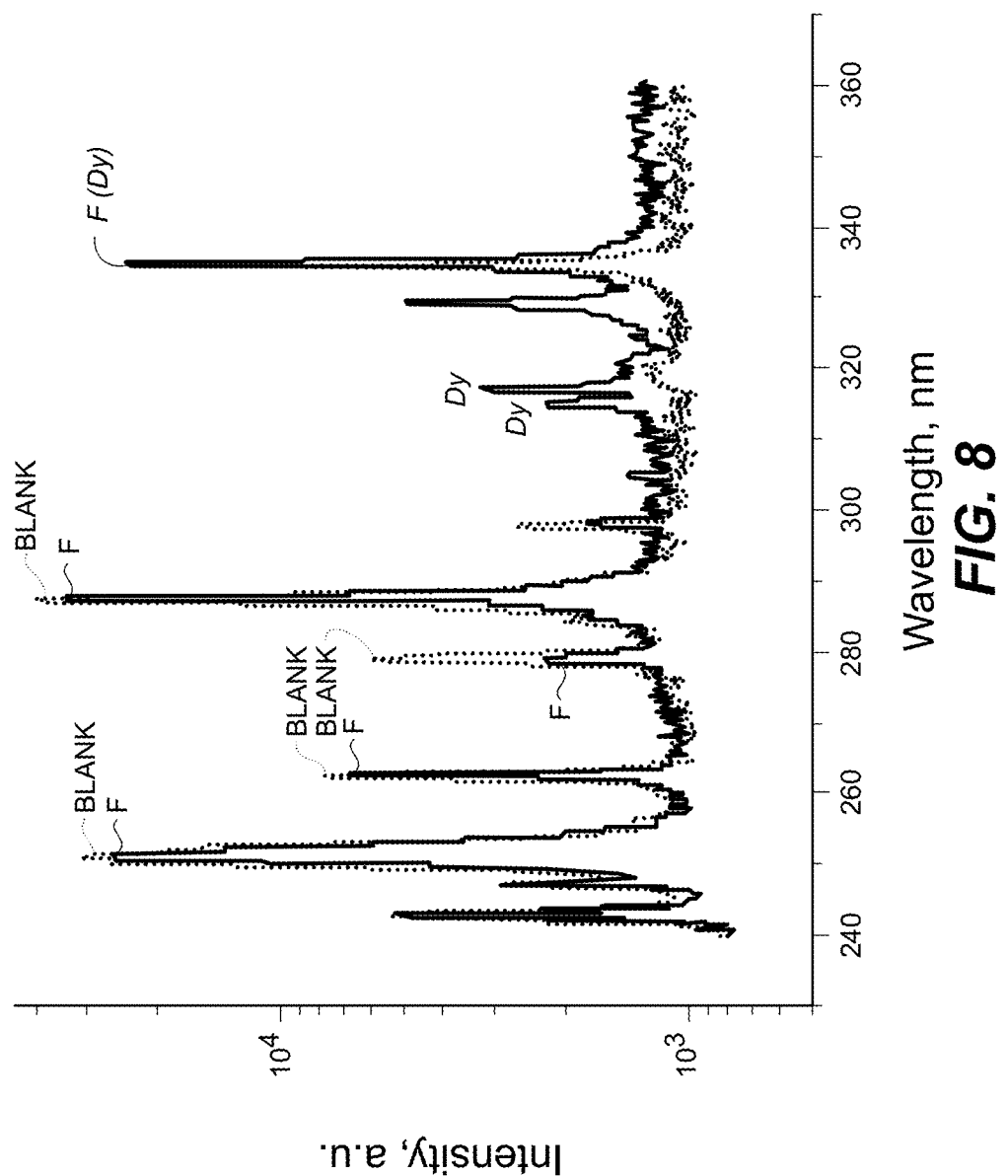
FIG. 8 is a plot showing spectral measurement of a sample containing antitoxin antibodies labeled with Dy in the 240-360 nm range according to one embodiment.

FIG. 8 is a plot showing spectral measurement of a sample containing antitoxin antibodies labeled with Dy in the 240-360 nm range.

Figure 9:
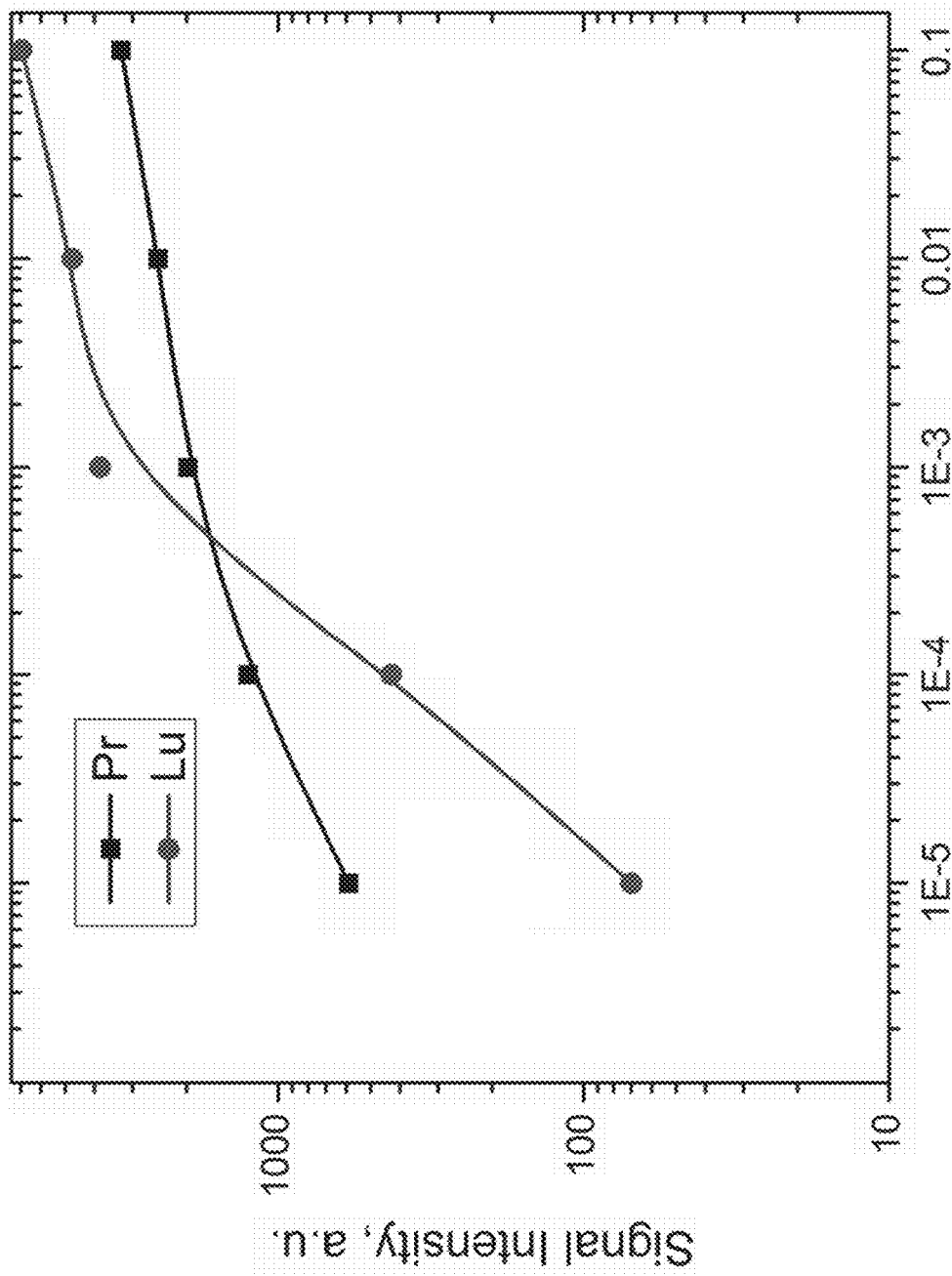
FIG. 9 is a plot showing initial dose response to two different agents, Shiga Toxin Stx-2-2 labeled with $^{141}$Pr and Ricin labeled with $^{162}$Lu.

FIG. 9 is a plot showing initial dose response to two different agents, Shiga Toxin Stx-2-2 labeled with $^{141}$Pr and Ricin labeled with $^{162}$Lu.

Figure 10:
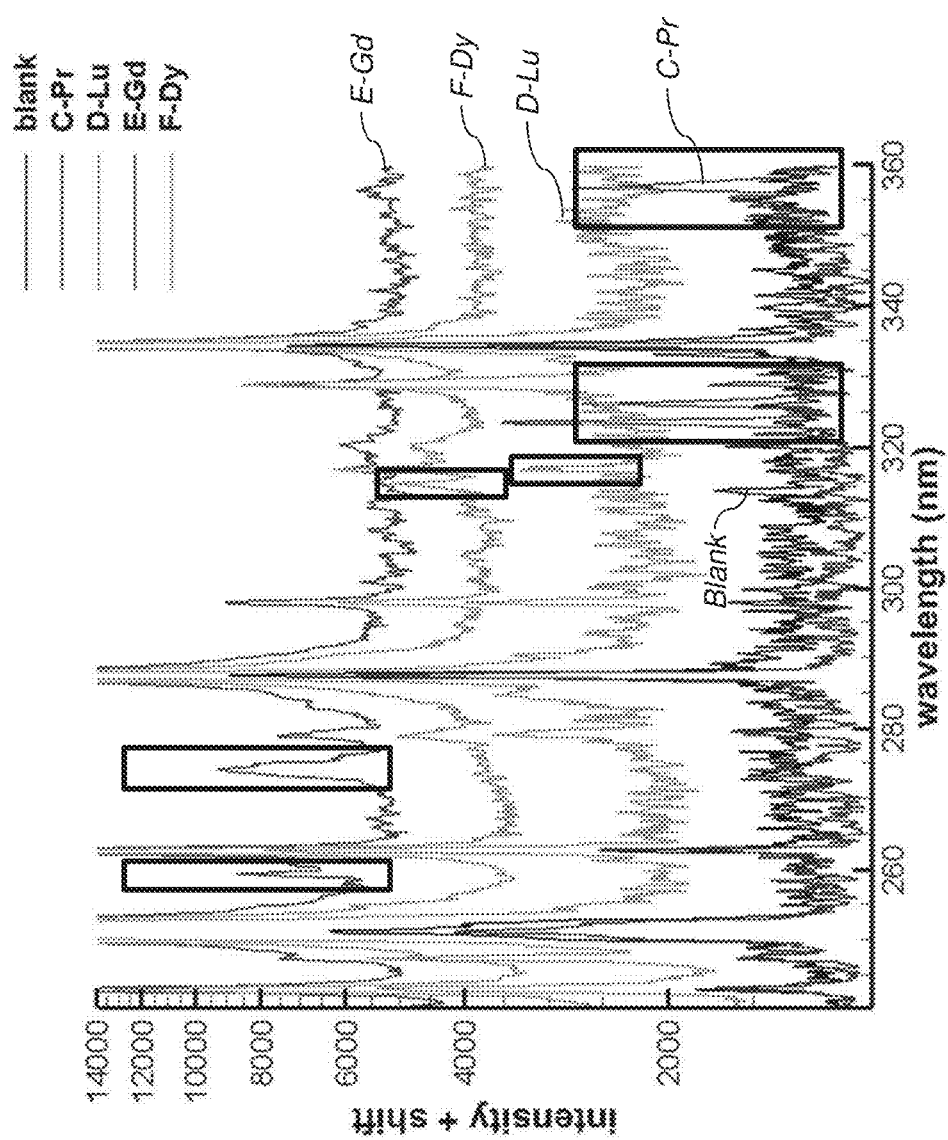
FIG. 10 is a plot showing spectral measurement of the 240 nm-360 nm window, where there are possible peaks that only exists on certain regions of the spectra (for Pr, Lu, Gd, and Dy).

FIG. 10 is a plot showing spectral measurement of the 240 nm-360 nm window, where there peaks can be identified on regions of the spectra representing Pr, Lu, Gd, and Dy simultaneously as shown.

Figure 11:
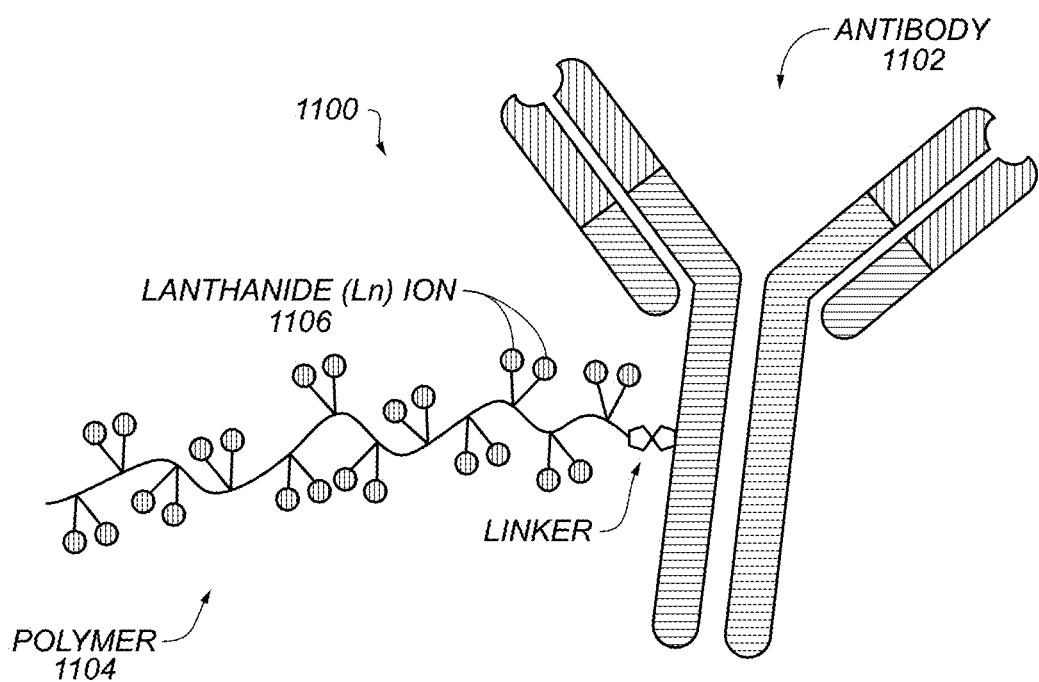
FIG. 11 is a high-level depiction of an example recognition construct.

FIG. 11 shows an example recognition construct 1100. An antibody 1102, e.g., a monoclonal antibody (mAb), includes or is linked (e.g., covalently attached) to a metal-chelating polymer 1104. In some examples, about 20 lanthanide ions 1106 bind to a single polymer chain. In some examples of multiple recognition constructs 1100, about 2.4 polymer chains bind to each antibody 1102, on average. In some cases different lengths and different numbers of polymers can be attached to the antibody. In some examples, the polymer-linked antibody can be prepared by anionic ring-opening polymerization. In some examples, more than one type of metal atom or ion 1106 can be included in recognition construct 1100. Using multiple metals can permit adjusting the spectra to increase multiplexing factor or reduce noise.

In some examples, monoclonal antibodies (mAbs) are tagged with various metallic elements via metal-chelating polymers which carry multiple copies of individual metal ions and provide a reactive functionality for attachment. Example ions can include at least one of $^{59}$Pr Praseodymium, $^{60}$Nd neodymium, $^{62}$Sm Samarium, $^{64}$Gd Gadolinium, $^{65}$Tb Terbium, $^{66}$Dy Dysprosium, $^{67}$Ho Holmium, $^{68}$Er Erbium, $^{69}$Tm Thulium, $^{70}$Yb Ytterbium, or $^{71}$Lu Lutetium.

Using specific antibodies and different lanthanides, multiple targets may be investigated simultaneously in one sample, e.g., Shiga toxin, ricin, and botulinum toxin. In some examples of detecting botulinum, mAbs can include F1-2 (2.3 mg/mL, 0.2 mL) and F1-51. Both of these bind the heavy chain of botulinum neurotoxin (BoNT) and can be used in a sandwich assay such as those described below with reference to FIGS. 23 and 24. In some examples of detecting Ricin, mAbs can include RBV-11 (1.7 mg/mL, 0.4 mL); RC-91 mL ascites; RF-5 1 mL ascites; TFT B194102701 (binds to the β-chain); or TAZ E12 3C11 (1.2 mg/mL 0.25 mL). These can be used in a sandwich assay such as those described below with reference to FIGS. 23 and 24. In some examples of detecting Shiga-like toxin 2 (SLT2), mAbs can include Stx 2-1, which binds the A subunit of an SLT2, and Stx2-2, which binds the B subunit. An example SLT2 is A1B5, i.e., has 5 B subunits to each A subunit (on average).

In some examples of system 101, FIG. 1, the sample 198 comprises a recognition construct such as construct 1100. The metal, e.g., ion 1106, can be included in or linked to the recognition construct 1100. In some examples, the recognition construct 1100 comprises at least an antibody, adNectin, or other scaffold described above with reference to system 101.

Figure 12:
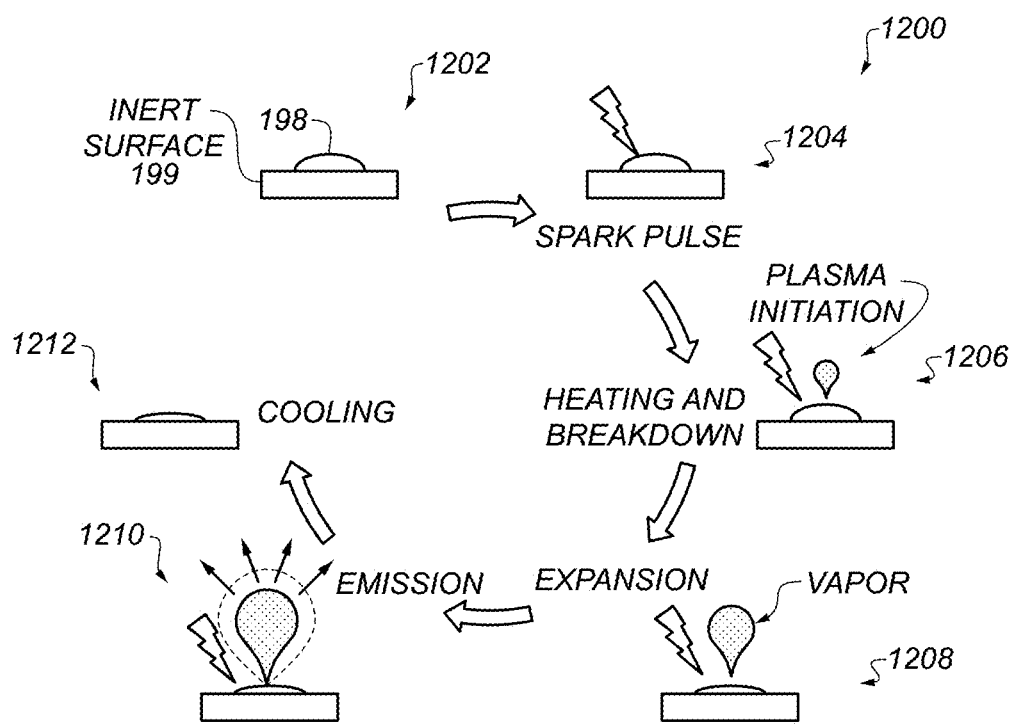
FIG. 12 illustrates an example process for analysis of a sample using spark-induced breakdown spectroscopy (SIBS).

FIG. 12 schematically illustrates an example process 1200 for analysis of a sample using SIBS. At 1202, sample 198 is applied to or disposed in or over substrate 199. At 1204, a spark pulse is applied to sample 198. At 1206, energy from the spark has begun to vaporize at least part of sample 198 to generate a vapor or plasma. In addition to or instead of initiating the breakdown process by a high-voltage spark, the plasma formation can induced using a laser, microwaves or glow-discharge microwave. At 1208, the vapor pulse has expanded and heated. At 1210, at least some of the plasma has become vapor and emits electromagnetic energy. The energy can be detected by spectroscopic detector 196, FIG. 1. At 1212, the sample has cooled and vapor or plasma has dissipated. In some examples, the substrate 199 can be reused beginning again at 1202.

Figure 13:
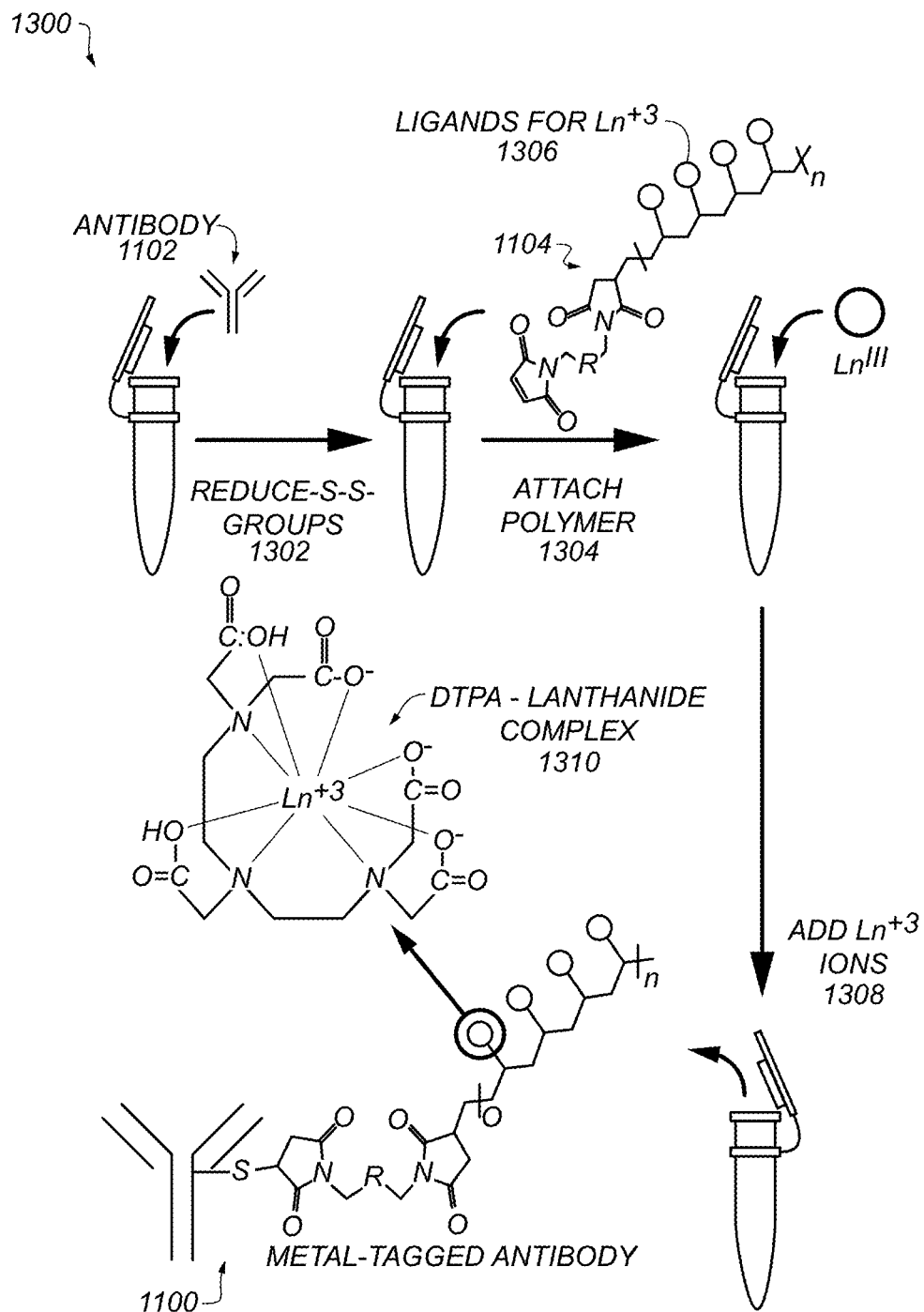
FIG. 13 illustrates an example process for preparing a recognition construct.

FIG. 13 schematically illustrates steps in a process 1300 of preparing a recognition construct such as construct 1100, FIG. 11. The illustrated construct 1100 includes an antibody 1102 tagged with ions, e.g., ions 1106, FIG. 11. Example process 1300 includes mAbs tagging with lanthanides to prepare compounds useful for label-based detection as described herein. In the illustrated example, diethylenetriaminepenta-acetic acid (DTPA) is used as a chelator to create high-affinity complexes with $Ln^{+3}$ ions.

The antibody 1102 of interest is placed in a reaction vessel, e.g., a test tube (as depicted). Antibody 1102 is subjected to selective reduction 1302 of —S—S— groups to produce reactive —SH groups. Polymer attachment 1304 is then carried out, which can include reacting the —SH groups with the terminal maleimide groups of polymer 1104 bearing metal-chelating ligands 1306 along its backbone. In some examples, the ligands 1306 include diethylenetriaminepenta-acetic acid (DTPA), which is used as a chelator to create high-affinity complexes with $Ln^{+3}$ ions. Other ligands 1306 can be used.

The polymer-bearing antibodies are purified, treated 1308 with, e.g., lanthanide ($Ln^{+3}$) ions, and then purified again. In some examples, the result is a complex 1310 of ligand 1306 and ion 1106. In some examples, process 1300 is used to prepare multiple constructs 1100, e.g., having respective, different types of antibodies 1102 and respective, different element labels (e.g., ions 1106). In some examples, each type of antibody is labeled with a different element.

In some examples, metal-chelating polymers (MCPs) such as polymer 1104 include a functional group enabling them to be covalently attached to biological macromolecules such as antibody 1102, and to concurrently binding multiple ions 1106 of metals. The illustrated reaction involves selective reduction of disulfide bonds in the hinge region of antibody 1102, followed by thiol addition to a maleimide group at one end of the polymer 1104.

FIGS. 14A-C illustrate measured data of examples of breakdown spectroscopy signals obtained from mAbs labeled with two different lanthanides and deposited on a silicon dioxide surface. The abscissas are wavelength in nm and the ordinates are intensity (in arbitrary units) measured by detector 196, FIG. 1.

FIG. 14A shows a measured spectrum of a silicon dioxide surface, e.g., of a clean silicon wafer substrate 199. The Si peaks provide alignment and calibration markers. For example, in a spectral measurement, the characteristic signal of silicon can be used to align and normalize multiple spectra so that the Si peaks coincide in a normalized space. The unique spectra of the metal ions can be defined by presence or absence of spectral features. In FIGS. 14B and 14C, for clarity of illustration, the silicon peaks are masked by vertical rectangles to show the remaining spectral features.

FIG. 14B shows a measured spectrum of a silicon wafer substrate 199 bearing recognition constructs such as constructs 1100. The recognition constructs in this example included mAb antibodies Stx 2-2 against SLT2 and were labeled with $^{141}$Pr.

FIG. 14C shows a measured spectrum of a silicon wafer substrate 199 bearing a different recognition construct. The recognition construct included mAbs Stx 2-1 against SLT2 and was labeled with $^{175}$Lu. As shown, the pattern of peaks differs between FIGS. 14A and 14B, permitting distinguishing Stx 2-2 from Stx 2-1, and thus permitting distinguishing A and B subunits of an SLT2.

Figure 15:
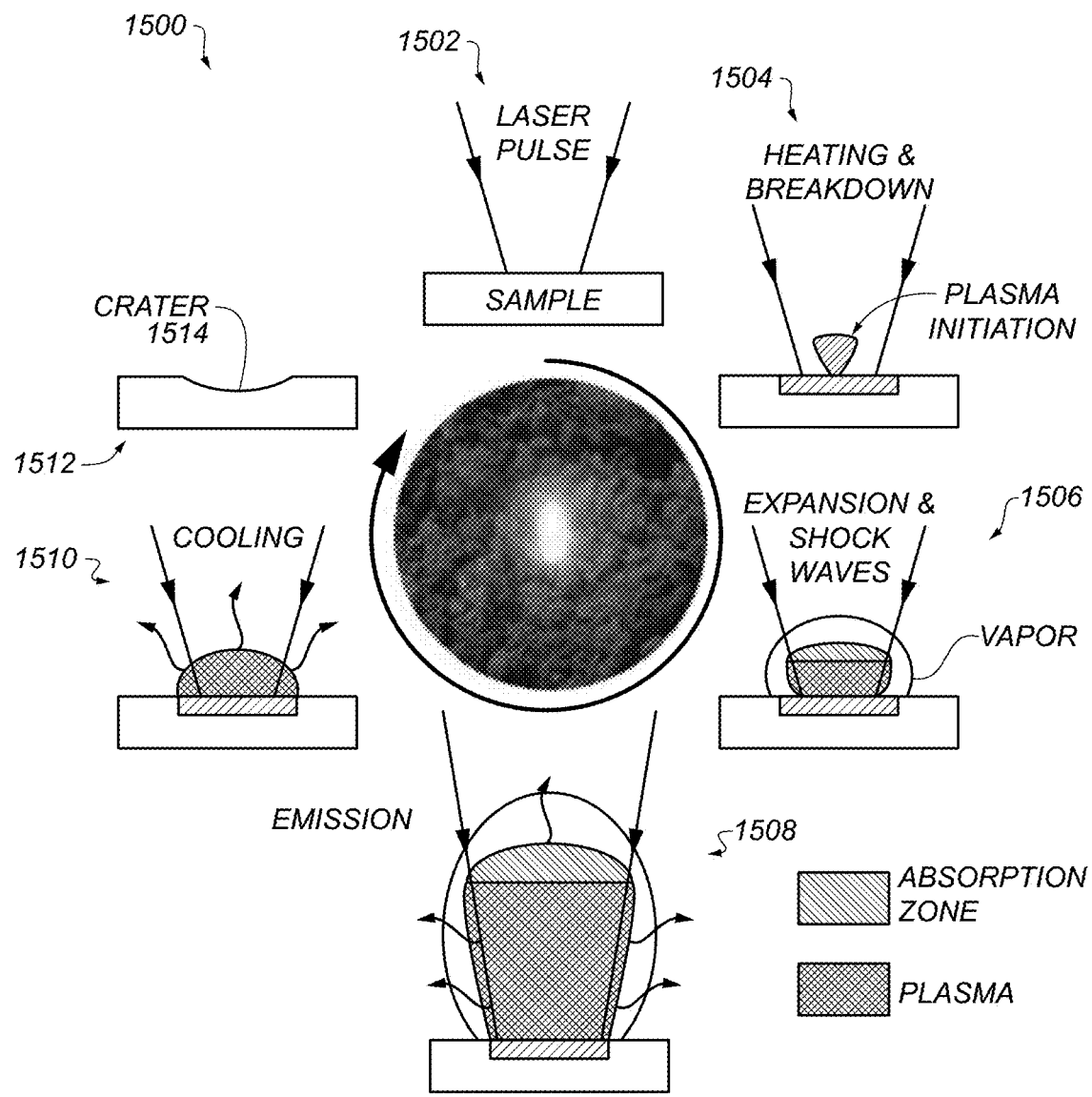
FIG. 15 schematically illustrates an example process for analysis of a sample using laser-induced breakdown spectroscopy (LIBS).

FIG. 15 schematically illustrates an example process 1500 for analysis of a sample using laser-induced breakdown spectroscopy (LIBS). At 1502, a pulsed laser beam is focused onto, or otherwise directed to irradiate, a sample of a substance to be analyzed. The sample can be on a substrate, or can be a solid-phase sample without a substrate. At 1504, the energy applied to the sample is sufficient to cause the sample to begin to evaporate. At 1506, the material vapor and the surrounding atmosphere form a plasma. At 1508, the material constituents of the plasma are excited and spontaneously emit electromagnetic radiation. This emission is resolved spectrally and is detected by a spectrometer, e.g., detector 196. At 1510, the plasma cools, resulting in substrate 1512 having crater 1514. Substrate 1512 can be disposed, or can be reused.

FIGS. 16A-16H schematically illustrate an example process for analysis of a sample using SIBS. Each of FIGS. 16A-16H is labeled with an example time from the beginning of the irradiation ("S" for seconds).

FIG. 16A shows laser beam LB irradiating sample S, which can be, e.g., in or over a substrate 199, FIG. 1. FIG. 16B shows material H heated by the electromagnetic radiation from laser beam LB. FIG. 16C shows a vapor bubble forming. FIG. 16D shows further heating of the vapor to form a plasma, which then emits electromagnetic radiation. FIG. 16E shows further emission, approximately 45 ns after the onset of emission. This 45 ns emission time can be sufficient to capture an optical measurement. FIG. 16F shows that, even after 5 µs, some emission is still present. FIG. 16G shows that, even after 20 µs, a small amount of emission remains. The long duration of emission can permit using a variety of spectroscopic detectors 196, e.g., less-expensive, longer-integration-time detectors 196 for portable uses such as in-the-field food testing, or more-expensive, shorter-integration-time detectors 196 for benchtop or high-throughput-screening uses. FIG. 16H shows particles PT escaping from the sample, in which a crater CR has been formed.

Figure 17A:
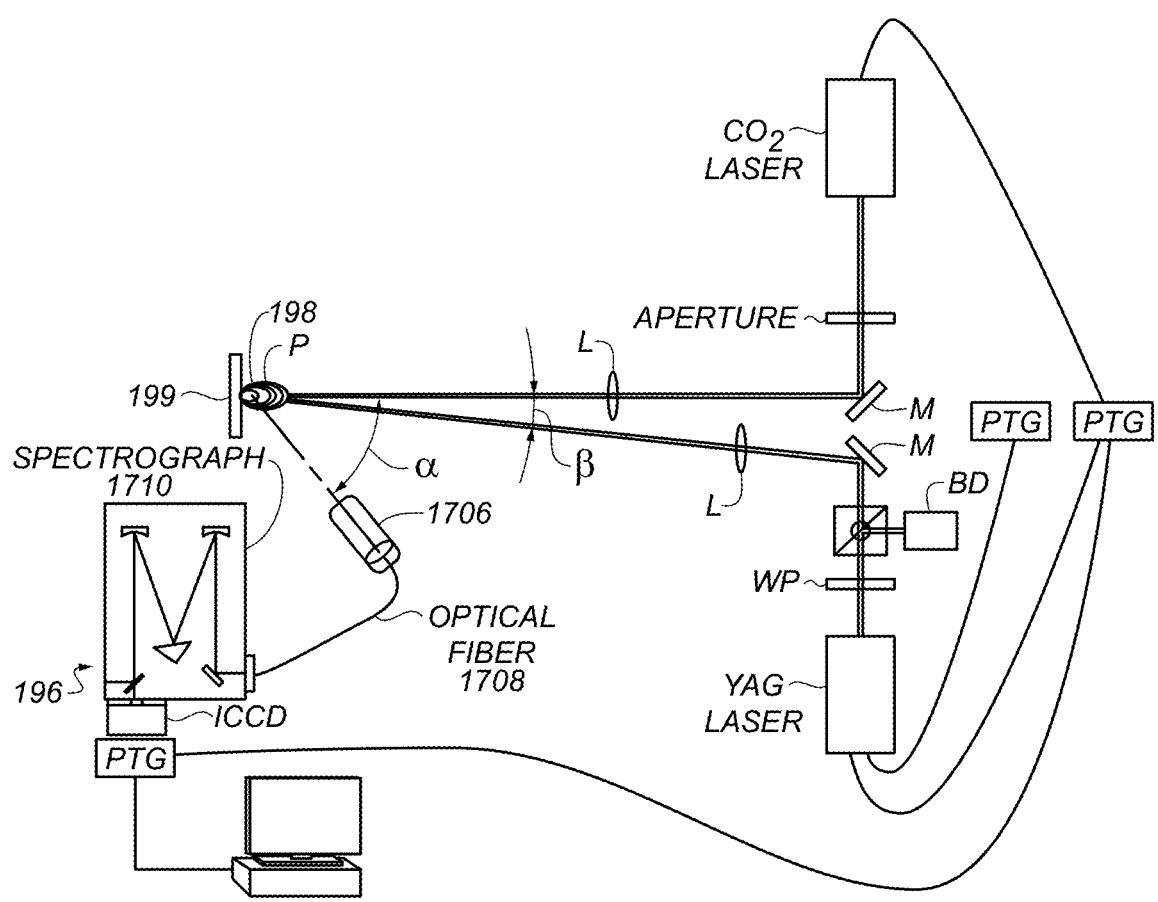
FIG. 17A is a schematic of a LIBS system.

FIG. 17A is a schematic of a system 1700 according to various aspects. System 1700 includes $CO_2$ laser 1702 and Nd:YAG ("YAG") laser 1704 driven by programmable timing generators PTG. Laser light is directed through one or more apertures, mirrors M, waveplates WP, cube beam-splitters (between WP and M), lenses L, or other optical, optoelectronic, or optomechanical components in order to direct energy to sample 198 on substrate 199. In some examples, at least some energy, e.g., of a non-desired polarization, is directed to beam dump BD. In some examples, angle β between incident beams is substantially equal to 5°.

Electromagnetic energy from lasers 1702 or 1704 irradiates sample 198 on substrate 199, producing plasma plume P. Optical collector 1706, e.g., a lens, passes at least some electromagnetic radiation from plasma plume P through optical fiber 1708 to spectrograph 1710 of detector 196. In some examples, angle α between one incident beam and the angle of detection of collector 1706 is 50°. Detector 196 detects electromagnetic radiation (e.g., the intensity thereof) as a function of wavelength, e.g., continuously or in discrete bins. For example, spectrograph 1710 can spatially disperse electromagnetic radiation carried by optical fiber 1708 across the surface of an intensified charge-coupled device (ICCD) linear or area sensor, and read the resulting intensity distribution at the active surface of the ICCD.

Figure 17B:
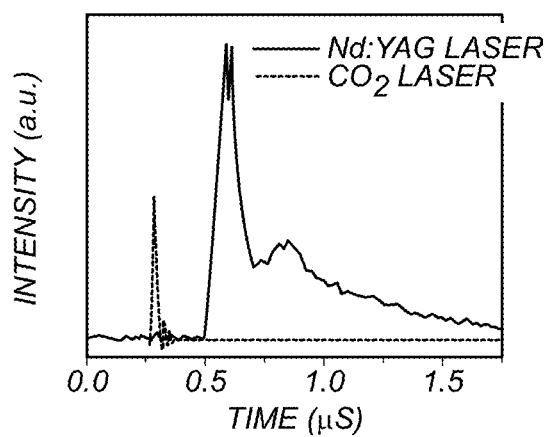
FIG. 17B is a plot of measured temporal profiles of example laser pulses.

FIG. 17B shows temporal profiles of Nd:YAG and CO2 laser pulses. The abscissa is time and the ordinate is intensity in arbitrary units. As shown, the Nd:YAG laser has a longer, more intense pulse, and the $CO_2$ laser has a shorter, less intense pulse. In some examples, the $CO_2$ laser can be used for precisely-timed excitation and the Nd:YAG laser can be used to supply higher amounts of excitation energy.

Figure 18:
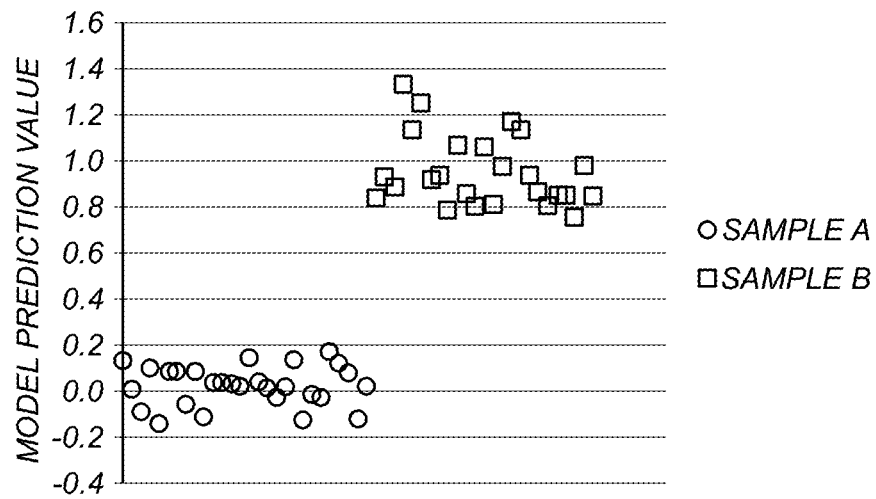
FIG. 18 illustrates example validation spectra prediction results.

FIG. 18 illustrates example results. Sample A is an *S. aureus* LP9, and Sample B is an *E. coli* DH5α. As shown, the samples can be readily distinguished with this type of plot.

Figure 19:
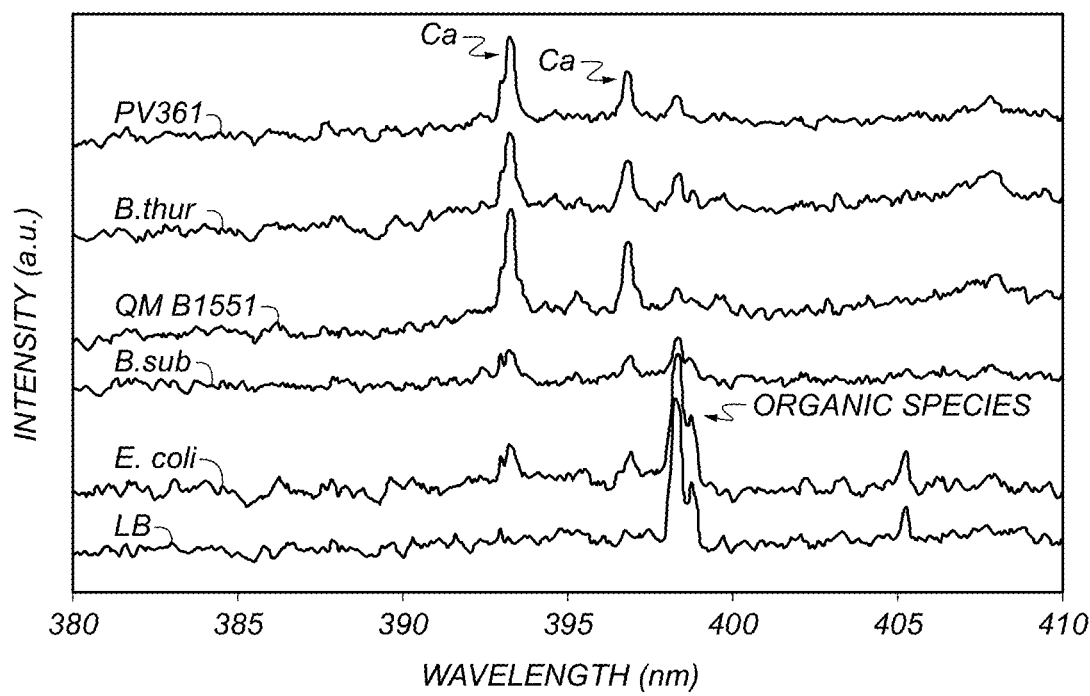
FIG. 19 illustrates example spectral measurements according to the prior art.

FIG. 19 illustrates example spectral measurements according to the prior art, with intensity (a.u.) as a function of wavelength. Illustrated are the LIBS spectra from 380 to 410 nm for *B. megaterium* PV361, *B. thuringiensis*, *B. megaterium* QM B 1551, *B. subtilis*, *E. coli*, and LB (a culture medium). The emission peaks at 393.7 and 396.9 nm are attributed to calcium atomic transitions. However, the peaks are not strong and have a significant overlap between different organisms.

Figure 20B:
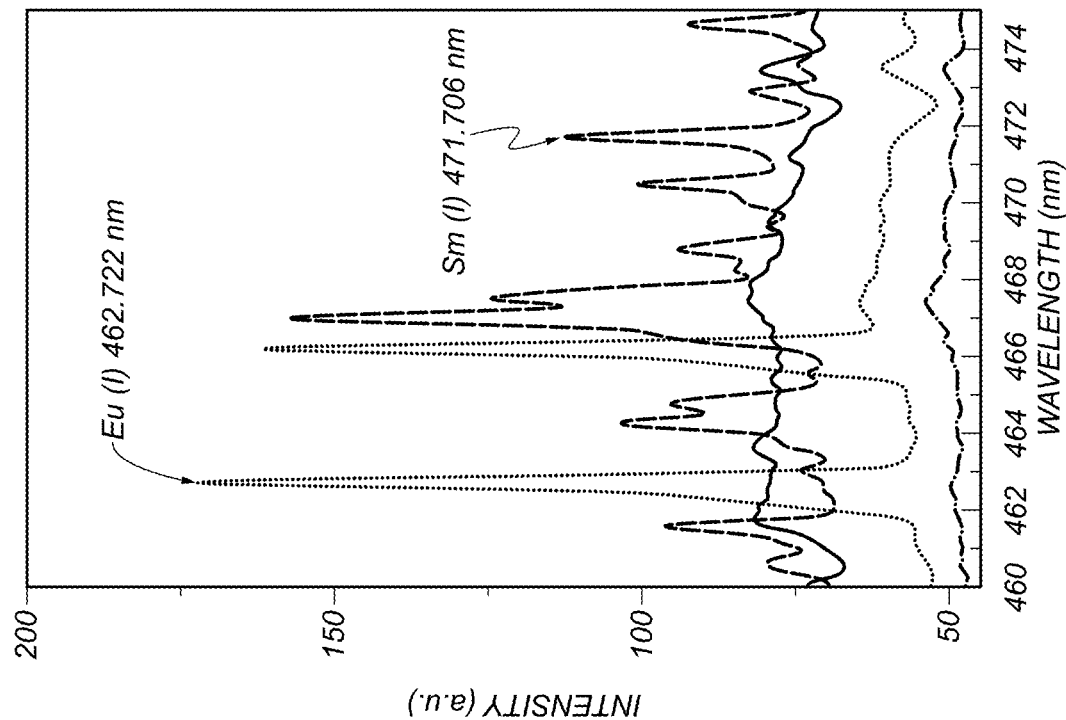
FIG. 20B illustrates example spectral measurements.
Figure 20A:
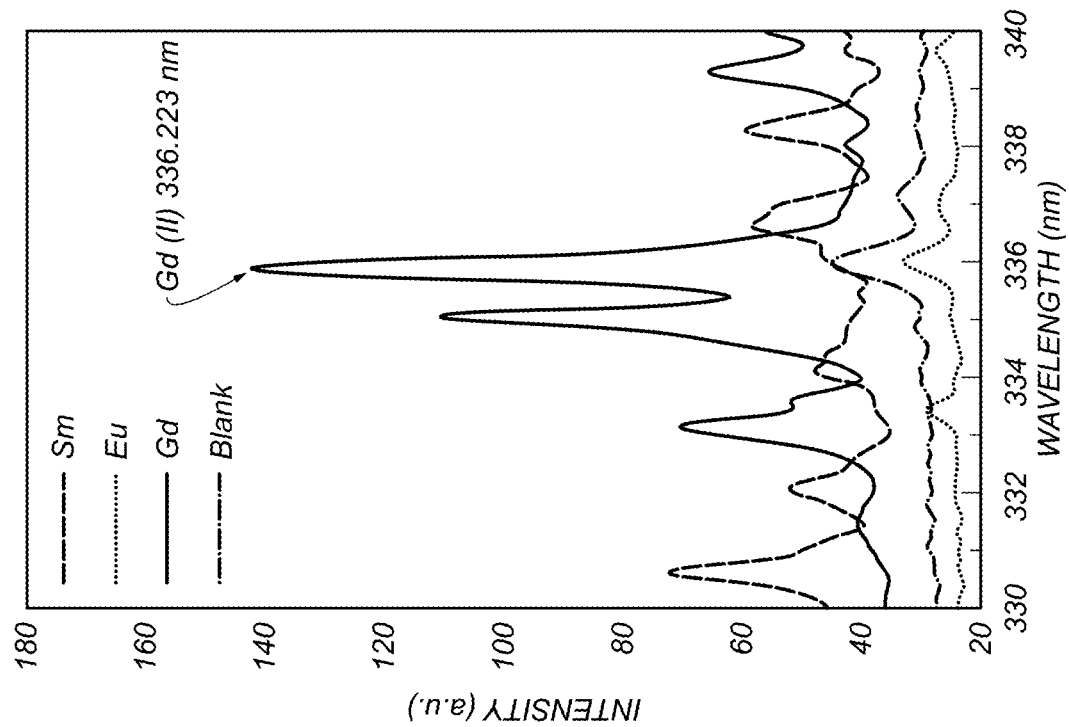
FIG. 20A illustrates example spectral measurements.

FIG. 20A illustrates example measurements of LIBS detection of Gd in an aqueous solution.

FIG. 20B illustrates example measurements of LIBS detection of Eu and Sm in an aqueous solution.

FIGS. 20A and 20B show that rare earth elements can be effectively distinguished from each other in LIB S measurements.

Figure 21:
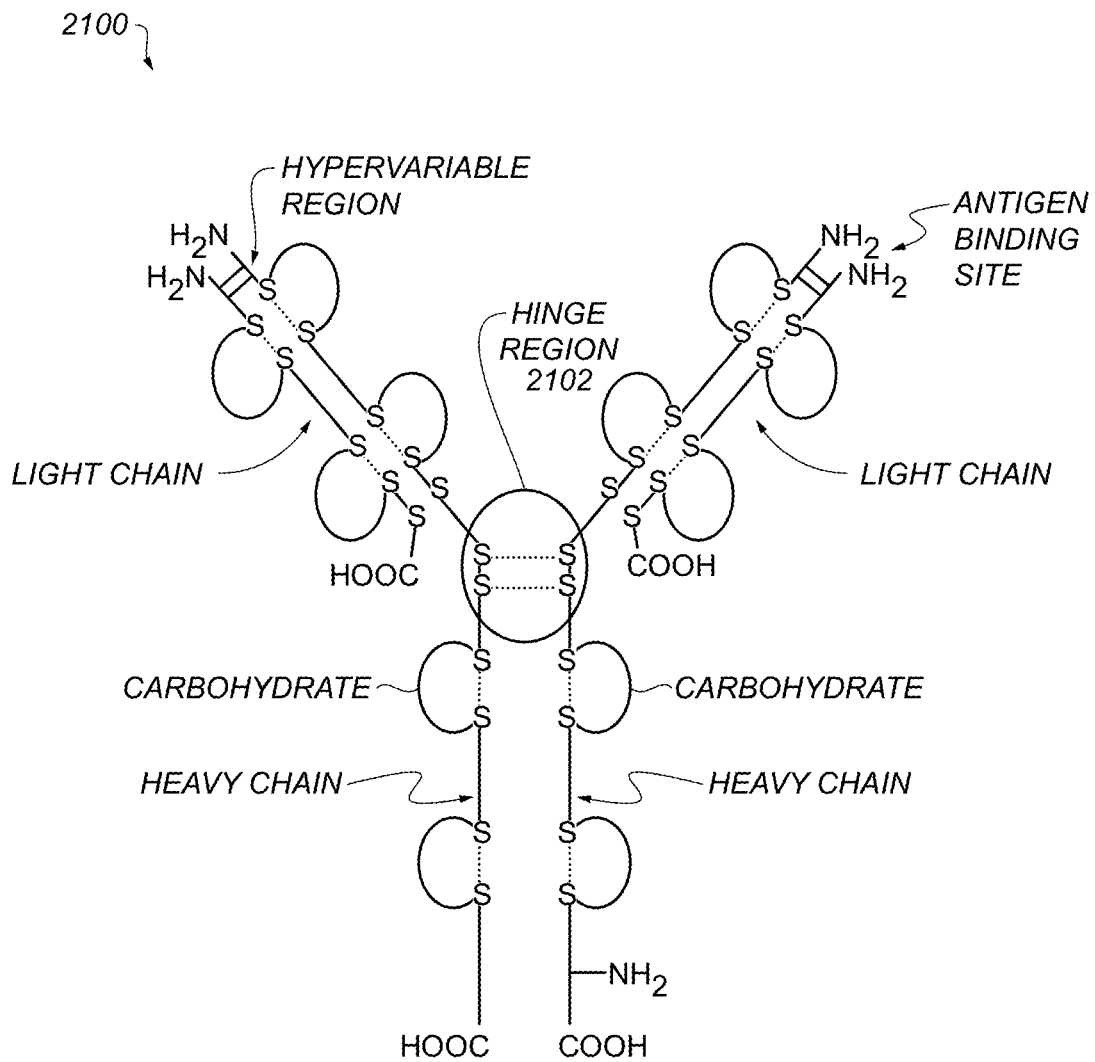
FIG. 21 graphically depicts structural components of an antibody useful with various examples.

FIG. 21 illustrates structural details of an example antibody 2100, which can represent construct 1100, FIG. 11. In some examples, a maleimide group of a polymer 1104, FIG. 11, can connect to the amino acid cysteine in the hinge region 2102 of the antibody 2100. The exact area where polymer 1104 bonds to antibody 2100 does not affect specificity of the antibody, in some examples.

Figure 22:
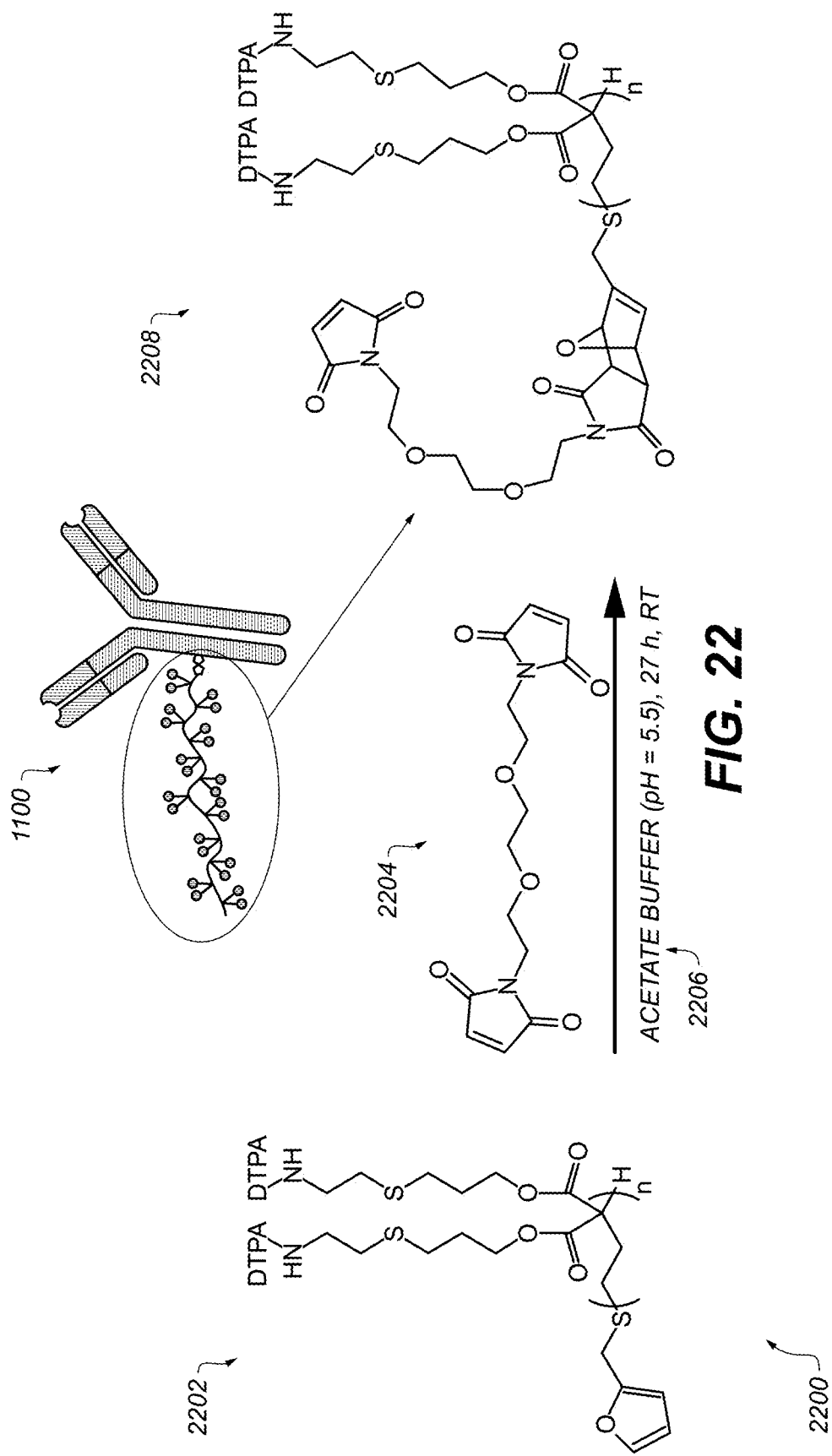
FIG. 22 schematically illustrates a process of preparing a recognition construct including a metal-tagged antibody.

FIG. 22 schematically illustrates steps in a process 2200 of preparing a recognition construct 1100 including a metal-tagged antibody. Compound 2202 is reacted with compound 2204 in an acetate buffer, e.g., pH=5.5, during operation 2206 to form compound 2208. Operation 2206 can be performed, e.g., at room temperature for 27 hours.

Process 2200 is an example of Diels-Alder End-Group Functionalization between the DTPA-containing polymer (compound 2202) and the bismaleimide reactive group (compound 2204) added at the end of the polymer. Once compound 2208 is formed, it can be reacted with antibody 1102 via mild reduction of disulfide bonds of the antibody 1102, using tris(2-carboxyethyl)phosphine (TCEP) to convert the reduced antibody, to form construct 1100.

Figures 23A, 23B, 23C:
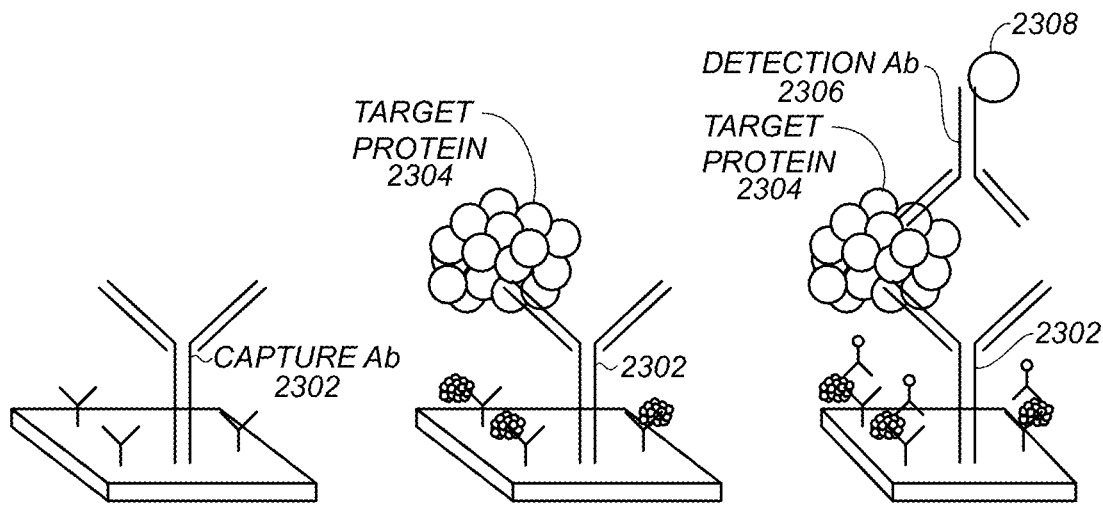
FIGS. 23A-23C schematically illustrate steps in a process of analyzing a sample.

FIGS. 23A-C schematically illustrate steps in a process of analyzing a sample. The illustrated process is a sandwich assay, in which an inert surface is functionalized and covered with recognition macromolecules. The biological specimen is added and the antigens of interest are captured by the surface-bound recognition macromolecules. Finally, the metal-tagged mAbs are added, binding to the immobilized antigen.

FIG. 23A shows capture antibody 2302 attached to a substrate, e.g., substrate 199, FIG. 1. In some examples, capture antibodies 2302 are immobilized on substrate 199 by the carbodiimide reaction: substrate 199, e.g., polystyrene or silica microbeads, prefunctionalized with carboxyl groups, are activated with equimolar concentration of 1-Ethyl-3-[3-dimethylaminopropyl]carbodiimide (EDC or EDAC) and N-hydroxysulfosuccinimide (Sulfo-NHS) or N-hydroxysuccinimide (NETS). Activation stabilizes the amine-reactive intermediate by converting it to a semistable amine-reactive sulfo-NHS or NHS ester. Then excess of antibody-protein is added for a reaction time of, e.g., 30 min-2 h. Remaining active groups can then be quenched with BSA, glycine or ethanolamine solution.

FIG. 23B shows a target protein 2304 that has been captured by capture antibody 2302. Target protein 2304 represents a target, e.g., a pathogen or toxin. Non-captured components or solutions can be washed off the substrate to reduce measurement noise.

FIG. 23C shows detection antibody 2306 bound to target protein 2304. Detection antibody 2306 is part of a recognition construct 1100 that also includes metal tag 2308. Metal tag 2308 can be vaporized as described above, e.g., with reference to FIG. 12 or 16, to provide detectable electromagnetic energy.

In some examples, the substrate, tagged with the relevant antibody, is incubated with the mixture of detection mAbs labeled with metal ions and a solution obtained from a filtered sample. In these examples, FIGS. 23B and 23C can take place concurrently. For example, time of incubation can be approximately 20-30 min at room temperature.

Figure 24:
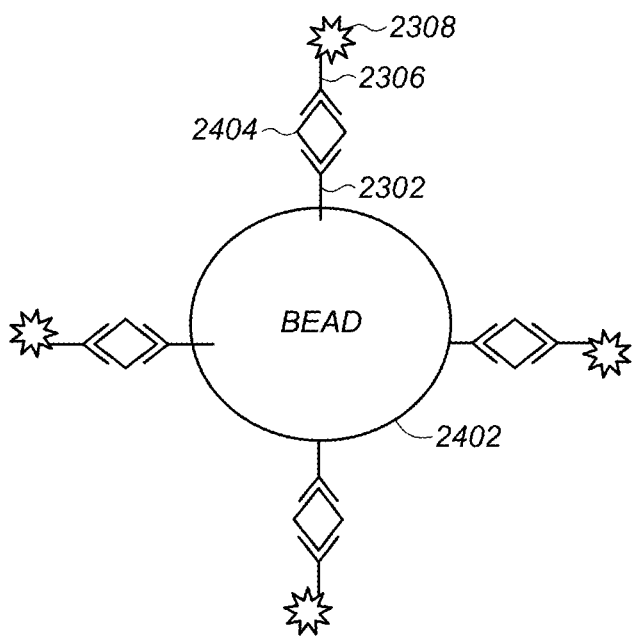
FIG. 24 is a schematic diagram of a bead carrying capture antibodies.

FIG. 24 is a schematic diagram of a bead 2402 carrying capture antibodies 2302, depicted as "Y" shapes attached to the bead 2402. Bead 2402 can include a silicon or polyester bead. Using beads rather than a flat surface can increase surface area, enhancing the assay sensitivity. Tagged antibodies can be immobilized on the surface of microbeads by the standard carbodiimide reaction. Polystyrene or silica microbeads prefunctionalized with carboxylic acid groups can be activated by an equimolar amounts of [1-ethyl-3-(3-dimethyl-aminopropyl) carbodiimide hydrochloride]. Sample can be brought into contact with the antibodies as discussed above with reference to FIG. 23. The capture antibodies are thus bound to targets 2404 of interest (depicted as diamonds) in the sample. Metal-tagged detection antibodies 2306 (depicted "Y" shapes with attached starbursts) are also bound to the targets. Metal tags 2308 (depicted as starbursts) can then be vaporized to provide detectable electromagnetic radiation.

The examples in FIGS. 23 and 24 are sandwich assays, though direct-detection assays can also be performed. In some examples, substrate 199 includes or is located in a plastic dish holding the capture antibody. Example solid substrates can include plastic or glass, and can be shapes as a sheet; filter, bead, or other shapes. Some examples use heavy-metal tagging and a washing (or other background removal) step. Compared to prior schemes using fluorescent or color change (colorimetric) assays, SIBS or LIBS assays as described herein can provide more accurate, more rapid measurements.

In some examples of assays described herein, data was collected in the 340 nm-460 nm range. A silicon wafer with no sample exhibited a strong peak at ~390 nm. A sample of phosphate-buffered saline (PBS) on the silicon wafer did not substantially change the position of the Si peak. A sample of Shiga toxin Stx 2-2 using a $^{141}$Pr label showed strong peaks at ~395 nm and ~420 nm, plus the Si peak. A sample of Ricin using a $^{162}$Dy label showed strong peaks at ~388 nm and ~395 nm, plus the Si peak. The difference in the peak patterns permits distinguishing tags using optical data (e.g., using only optical data), and thus permits distinguishing targets tagged with recognition constructs having different tags, e.g., different metals.

Figure 25:
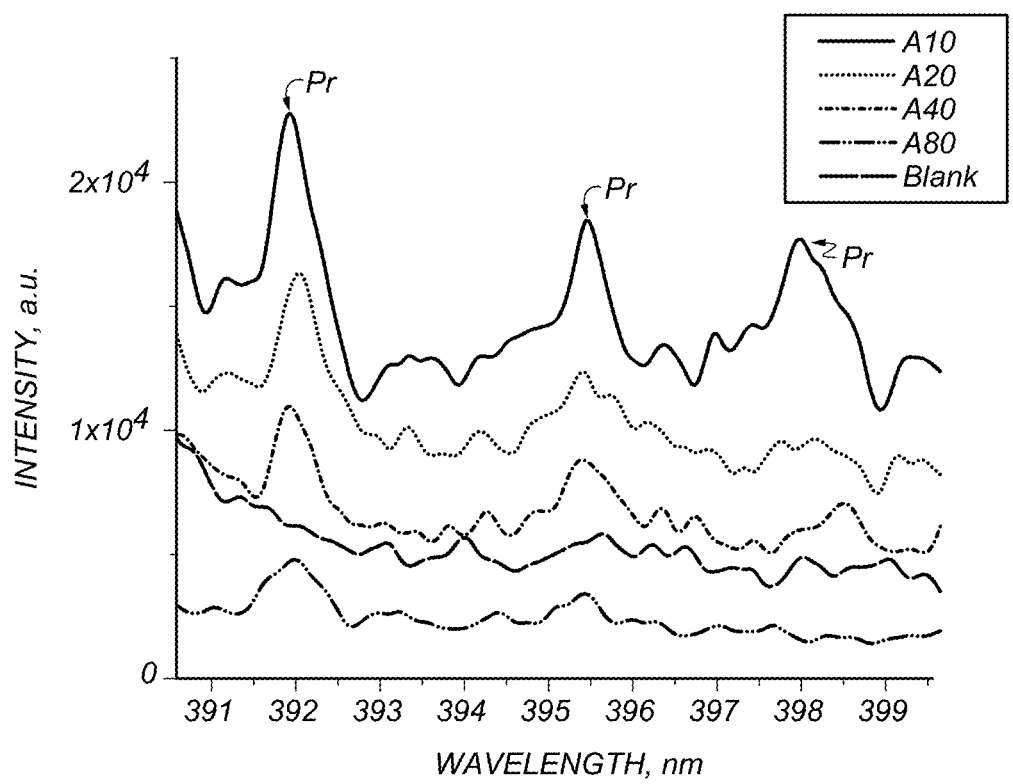
FIG. 25 is a plot of measured spectral data.

FIG. 25 illustrates measured spectral data. As shown, three wavelength peaks of a Pr tag are clearly visible.

Figure 26:
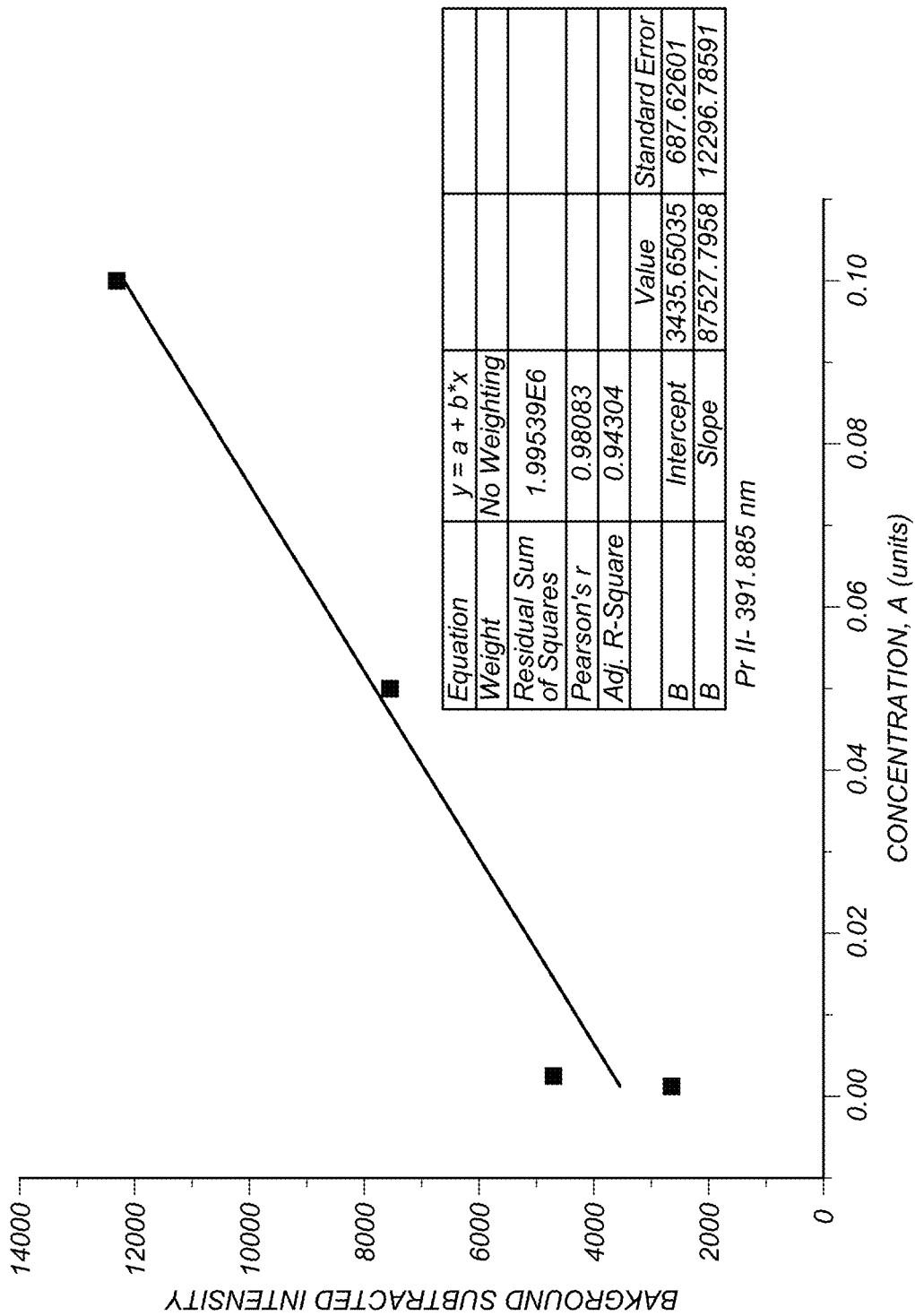
FIG. 26 is an example dose-response curve.

FIG. 26 illustrates an example dose-response curve determined based on measurements in the 320 nm-450 nm window using heavy metal Pr as a tag. FIG. 26, in the inset, shows statistical properties of the illustrated fit line to the illustrated measured data points (squares).

Figure 27:
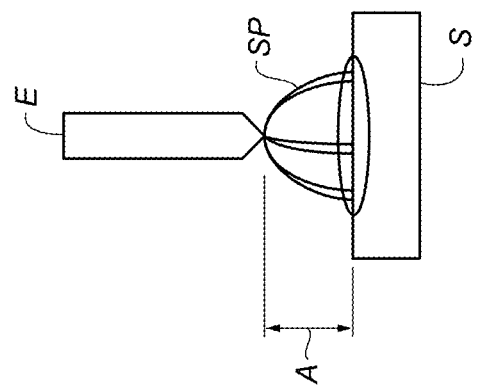
FIG. 27 is a schematic diagram of portions of a SIBS system.

FIG. 27 illustrates an example of application of energy to a sample, e.g., using SIBS. Voltage is applied between an electrode E and a substrate S to create one or more sparks SP that strike the sample, thereby applying the sparks to the sample, vaporizing the sample, and creating a plasma. It is not necessary that the spark directly ionize the sample; heat or electromagnetic radiation emitted by the spark can also contribute to plasma formation. In some examples, distance A is ~3 mm-~5 mm and the crater is ~5 mm in diameter. Configurations such as that depicted can interrogate, in one measurement, a relatively large sample area. This can increase the throughput of measurements. Increasing throughput can be useful, e.g., in field tests for contamination of food or water.

Figure 28:
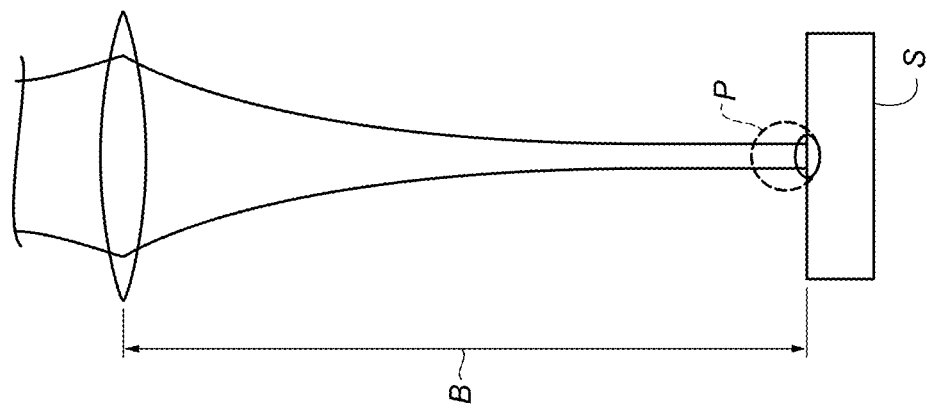
FIG. 28 is a schematic diagram of portions of a LIBS system.

FIG. 28 illustrates an example of application of energy to a sample, e.g., using LIBS. A laser beam is focused on a substrate S to create a plasma P of a sample. In some examples, distance B between the lens and the sample is ~200 mm-~1500 mm, and the crater is ~100 μm in diameter. Configurations such as that depicted can interrogate, in one measurement, a relatively small sample area. This can increase the precision of measurements. Increasing precision can be useful, e.g., in laboratory tests.

FIG. 29 illustrates an example 2900 of application of energy to a sample, e.g., using SIBS. Substrate 2902 holds sample 2904. Electrical supply 2906, e.g., under control of processor 186, FIG. 1, applies voltage or current pulses to electrodes 2908, 2910 to cause the air, sample, other substances, or vacuum between electrode 2908 and electrode 2910 to become conductive (e.g., break down), forming spark 2912. Spark 2912 can pass directly through at least some of sample 2904, or (as shown) can travel in proximity to sample 2904. Energy from spark 2912 can be provided to sample 2904 to transform at least part of sample 2904 into a plasma. Example forms of energy from spark 2912 can include, e.g., kinetic energy of ionized air or sample within spark 2912, electromagnetic energy radiated by spark 2912, or thermal energy conducted from spark 2912 to substances around it, such as sample 2904.

FIG. 30 shows a flowchart illustrating an example process 3000 for analyzing a sample. Some examples permit characterizing a target, e.g., a biological target, within a sample. The steps can be performed in any order except when otherwise specified, or when data from an earlier step is used in a later step. In at least one example, processing begins with step 3002. For clarity of explanation, reference is herein made to various components shown in FIGS. 1-29 that can carry out or participate in the steps of the example method. It should be noted, however, that other components can be used; that is, example method(s) shown in FIGS. 30 and 31 are not limited to being carried out by the identified components.

At 3002, a recognition construct is applied to the sample. The recognition construct can include a metal and a scaffold, e.g., a biological scaffold. The scaffold can be configured to bind to the target. Examples are discussed above with reference to FIGS. 11, 13, and 21-24. In some examples, the recognition construct can consist of at least one metal or salt. In some examples, the recognition construct can exclude, i.e., can be substantially free from, one or more, or all, of the following: adNectins, iMabs, anticalins, microbodies, peptide aptamers, designed ankyrin repeat proteins (DARPins), affilins, tetranectins, or avimers.

In some examples, the sample can be free of one or more of the compound types listed in the preceding paragraph. For example, the sample can exclude antibodies, or can exclude recognition constructs such as recognition construct 1100, FIG. 11. In some examples, the sample can include only antibodies (or other compound types listed in the previous paragraph) that are naturally occurring in the sample, as opposed to being added as described in step 3002.

In some examples, processing can begin with step 3004. In some examples, steps 3004 and 3006 can be performed, e.g., to test for the presence of metals, salts, or other distinguishable targets in the sample. As used herein, "distinguishable targets" are targets that, when suitably energized, emit electromagnetic radiation having an optical spectrum that can be identified in the collected optical-spectrum signal, e.g., using techniques discussed below with reference to step 3104. Samples of food, water, or other items useful to human biology, for example, can be measured as described with reference to steps 3004 and 3006, e.g., to test for lead or other heavy metals, or other contaminants, in those samples. Moreover, samples can be tested, e.g., for the presence of salts such as metal salts.

In some examples, a sample 198 can contain metal(s) (or other targets) included in recognition constructs added at step 3002, and can also contain metal(s) (or other distinguishable targets) present in the sample before step 3002, or otherwise present in the sample but not part of a recognition construct. Various examples herein can, in a single measurement, detect both targets in constructs 1100 and distinguishable targets outside of recognition constructs. This can permit, e.g., performing a single measurement of, e.g., a food or water sample, to test for both bacterial contamination (using recognition constructs that bind to bacterial species of interest) and heavy-metal contamination (the heavy metals themselves being distinguishable targets different from the metal ions 1106 used in the recognition constructs).

At 3004, energy is applied to the sample. The energy applied at step 3004 is sufficient to transform at least some of the sample into a plasma, e.g., to convert at least some of the sample from a solid, liquid, or gaseous phase to a plasma phase. Examples are discussed above with reference to FIGS. 12, 15, 16A-16H, 17, 27, and 28.

In some examples, step 3004 includes applying energy to the sample before adding recognition construct to the sample or without first adding recognition construct to the sample.

In some examples, the applying energy comprises heating at least part of the sample, e.g., using a flame, resistive heater, inductive heater, or other heat source. In some examples, the applying energy comprises irradiating at least part of the sample using a laser. Examples are discussed above, e.g., with reference to FIG. 15 or 28. In some examples, the applying energy comprises applying a spark to at least part of the sample. For example, a spark can be generated between an electrode and a substrate retaining the sample, e.g., as in FIG. 12 or 27. In another example, a spark can be generated between two electrodes in proximity to the sample, e.g., as discussed above with reference to FIG. 29. In some examples, multiple sparks can be applied to provide sufficient energy to the at least part of the sample to form a plasma emitting a detectable amount of electromagnetic radiation.

At 3006, electromagnetic radiation emitted by the plasma is detected to provide an optical-spectrum signal of the sample. Wavelength-specific peaks in the optical-spectrum signal, or other characteristics of the detected electromagnetic radiation as a function of wavelength, can be correlated with the metal in the recognition construct. Examples are discussed above with reference to FIGS. 12, 15, 16A-16H, and 17.

FIG. 31 shows a flowchart illustrating an example method 3100 for analyzing a sample according to various aspects. The sample can be analyzed to determine presence of a target. Processing can begin at step 3102.

At step 3102, a recognition construct is prepared. Some examples include preparing the recognition construct including a tagged scaffold. Examples are discussed above, e.g., with reference to FIG. 11, 13, 21, or 22.

In some examples, step 3102 can include preparing the recognition construct by bonding a metal to a scaffold. Examples are discussed above, e.g., with reference to FIG. 11, 13, 21, or 22. The scaffold can include, e.g., a biological scaffold. The metal can include, e.g., a metal atom or ion. In some examples, the target includes a microbe and the scaffold comprises an antibody against epitopes present on a surface of the microbe. In some examples, the target includes a biological toxin and the scaffold comprises an antibody against the biological toxin. Step 3102 can be followed by step 3002.

In some examples, e.g., of analyzing food or water samples as described above with reference to FIG. 30, processing can begin at step 3004. Measurements can be taken as described above with reference to steps 3004 and 3006. At least one of steps 3002, 3004, or 3006 can be followed by step 3104.

At step 3104, presence of the metal in the sample is determined based at least in part on the optical-spectrum signal. Step 3104 can include, e.g., performing at least one of spectral unmixing, constrained energy minimization (CEM), pattern recognition, or classification. Various examples of step 3104 can provide rapid processing of complex optical spectra originating from label-free and label-based measurements. For example, given a library of possible spectra of constituents of the sample, spectral unmixing can be used to determine the most likely proportions of those constituents. In other examples, blind unmixing can be used to estimate a most-likely collection of constituent spectra without reference to a library of spectra.

In some examples, readouts provided by systems described herein can include multispectral data sets. Let r denote the normalized vector of observations (digitized readouts from the spectrometer), M an L×p spectral-signature matrix (p being the number of metal labels used in the test, and L the number of bands employed in the spectrometer), and a the vector of fractional abundances of the j-th label in the measured sample. Also, let n denote noise. Therefore, for a measured sample, Eq. (1) holds.

$$r = Ma + n. \quad (1)$$

This simple mixture model assumes that a multiband spectrum measured from a sample can be expressed as a linear combination of the spectral signatures of the labels used and the intrinsic spectra of the biological material and matrix with appropriate fractions $a = [\alpha_1, \alpha_2, \ldots, \alpha_n]$. The physical constraints of spectral analysis require that an estimate of a be positive and that $\Sigma_{i=1}^{p} \alpha_i = 1$. Therefore, the constrained least-squares estimator of a is Eq. (2).

$$\hat{a} = \min_{a \in \Delta} \{(r - Ma)^T (r - Ma)\} \; s.t. \; \Delta = \left\{ a \middle| \left( \sum_{j=1}^{p} a_i = 1 \right) \wedge (a_i \geq 0) \right\}. \quad (2)$$

Consequently, multiplying the fractions vector â by the integral of the optical spectrum signal collected by the detector allows retrieval of the signals originating from every single label, as well as the signal of the matrix/unlabeled sample.

In some examples, the spectral constituents of a sample may not be completely known. Moreover, the signal of the unlabeled matrix may be unavailable. In such situations, blind unmixing of the labels can be performed.

Various aspects use constrained energy minimization (CEM) to determine a label of interest. CEM implements a finite-impulse response (FIR) filter in such a manner that the filter output energy is minimized subject to a constraint imposed by the desired spectral signature of interest. CEM does not assume the linear mixture model or any particular noise characteristics. An example CEM filter w is in Eq. (3). Other filters known in hyperspectral analysis can be used.

$$w_{CEM} = (d^T R_r^{-1} d)^{-1} R_r^{-1} d. \quad (3)$$

where R is the sample correlation matrix $R = \langle rr^T \rangle$.

A CEM-based filter as shown in Eq. (3) is designed to detect the desired target d while mathematically minimizing the filter output energy caused by other (presumably unknown) undesired signal sources. Various examples of CEM can obtain concentrations of single metallic labels of interest, producing a result substantially equal to a result of unmixing on the same measurements. For example, when the mixture is linear and the label of interest co-occurs with other labels in proportion to their global average concentrations in the tested material, CEM can accurately identify the metal tags by their spectra.

The CEM filter can be expanded to operate on multiplexed and multi-label assays. For instance, if a particular complex contaminant in a sample is defined by the presence of three chemical constituents and absence of two other markers, a CEM-based filter can be designed to produce a desired signature. Let F denote a multi-label signature F={$d_1$, $d_2$, $d_3$}. An example constraint for a CEM filter to detect the desired target F while mathematically minimizing the remaining signals is shown in Eq. (4).

$$\min_{w}\{w^T R_r w\} \text{ s.t. } F^T w = 1. \qquad (4)$$

The solution to Eq. (4) is a CEM-based filter w*:

$$w_{CEM}^* = R_r^{-1} F (F^T R_r^{-1} F)^{-1} 1. \qquad (5)$$

In some examples, step 3104 can include determining presence of the metal in the sample based at least in part on results of a multi-class classifier trained on training data including spectra of metals that may possibly occur in the sample. Example classifiers can include support vector machines, kernel estimators such as nearest-neighbor classifiers, decision trees or forests, or neural networks such as deep neural networks.

In some examples, step 3104 can include determining presence of the metal in the sample based at least in part on at least a non-fluorescence portion of the optical-spectrum signal. For example, the THERMOFISHER CELL-TRACKER Orange CMRA fluorescent dye has a fluorescent emission peak at approximately 578 nm and a full width at half-maximum (FWHM) of the emission spectrum of 42 nm (~560 nm-~602 nm). In some examples, step 3104 can include analyzing the portion outside the FWHM of a particular fluorescent emission, e.g., 450 nm-560 nm and 602 nm-750 nm. In some examples, step 3104 can include analyzing the full range of the captured spectrum, e.g., 450 nm-750 nm, or a spectral range wider than, e.g., 50 nm, 100 nm, 150 nm, 200 nm, or 250 nm. Analyzing portions of the spectrum that do not correspond to fluorescent dyes that may be present in a sample, or that are wider than the FWHMs of fluorescence peaks of such dyes, can permit distinguishing more tags from each other than some prior fluorescence-based schemes. Such analyses can additionally or alternatively reduce noise due to autofluorescence by the sample.

EXAMPLE CLAUSES

Various aspects can include at least one of the following provisions.

A: A method for characterizing a biological target within a sample, the method comprising: labeling the target with a biomolecular recognition construct; and measuring an optical-spectrum signal of the biomolecular recognition construct.

B: The method according to paragraph A, further comprising heating the labeled target before measuring the optical-spectrum signal.

C: The method according to paragraph A or B, further comprising measuring the optical-spectrum signal by performing laser-induced breakdown spectroscopy.

D: The method according to any of paragraphs A-C, further comprising measuring the optical-spectrum signal by performing spark induced breakdown spectroscopy.

E: The method according to any of paragraphs A-D, further comprising classifying data of the optical-spectrum signal using a computer-based classifier and assigning a classification score to the analyzed sample.

F: The method according to any of paragraphs A-E, further comprising preparing the biomolecular recognition construct by tagging a scaffold, e.g., a biological scaffold, with a metal atom or ion.

G: The method according to paragraph F, wherein the target includes a microbe, e.g., a bacterium, and the biological scaffold comprises an antibody against epitopes present on the surface of the microbe, e.g., the bacterial surface.

H: The method according to paragraph F or G, wherein the metal atom or ion comprises a heavy metal atom or ion.

I: The method according to any of paragraphs F-H, wherein the target includes a biological toxin and the biological scaffold comprises an antibody against the biological toxin linked to heavy metals.

J: A system for characterizing a target within a sample, the system comprising: an energy source configured to transform a metal in the sample into a plasma; and an optical spectroscopic detector configured to detect electromagnetic radiation emitted by the plasma and to provide an optical-spectrum signal corresponding to at least some of the electromagnetic radiation.

K: The system according to paragraph J, further comprising: a processor; and a memory, e.g., a processor-accessible memory or at least one computer storage medium, storing instructions executable by the processor to cause the processor to perform operations comprising determining presence of the metal in the sample based at least in part on the optical-spectrum signal.

L: The system according to paragraph K, the operations (e.g., the operations for determining) further comprising performing spectral unmixing or spectral fingerprint classification on the optical-spectrum signal.

M: The system according to paragraph K or L, the operations further comprising determining presence of a second metal in the sample based at least in part on the optical-spectrum signal, wherein the second metal is different from the metal.

N: The system according to any of paragraphs K-M, the operations further comprising determining presence of the metal in the sample based at least in part on at least a non-fluorescence portion of the optical-spectrum signal.

O: The system according to any of paragraphs K-N, the operations further comprising determining presence of the metal in the sample based at least in part on a portion of the optical-spectrum signal extending over a spectral range wider than at least one of 50 nm, 100 nm, 150 nm, 200 nm, or 250 nm.

P: The system according to any of paragraphs J-O, further comprising a substrate configured to retain the sample in operative arrangement with the energy source.

Q: The system according to paragraph P, wherein the substrate comprises silicon or polystyrene.

R: The system according to paragraph P or Q, wherein the substrate comprises recognition macromolecules.

S: The system according to any of paragraphs J-R, further comprising the sample, wherein the sample comprises: a scaffold; and the metal linked to the scaffold.

T: The system according to paragraph S, wherein the scaffold comprises at least one of an antibody, adNectin, iMab, anticalin, microbody, peptide aptamer, designed ankyrin repeat protein (DARPin), affilin, tetranectin, or avimer.

U: The system according to any of paragraphs J-T, wherein the metal is not a heavy metal.

V: The system according to any of paragraphs J-U, wherein the metal is not toxic to humans.

W: A method for characterizing a target within a sample, the method comprising: applying to the sample a recognition construct comprising a metal and a scaffold, wherein the scaffold is configured to bind to the target; applying energy to the sample, wherein the applied energy is sufficient to transform at least some of the sample into a plasma; and detecting electromagnetic radiation emitted by the plasma to provide an optical-spectrum signal of the sample.

X: The method according to paragraph W, wherein the applying energy comprises heating at least part of the sample.

Y: The method according to paragraph W or X, wherein the applying energy comprises irradiating at least part of the sample using a laser.

Z: The method according to any of paragraphs W-Y, wherein the applying energy comprises applying a spark to at least part of the sample.

AA: The method according to any of paragraphs W-Z, further comprising: determining presence of the metal in the sample based at least in part on the optical-spectrum signal by performing at least spectral unmixing or constrained energy minimization (CEM).

AB: The method according to any of paragraphs W-AA, further comprising: preparing the recognition construct by bonding the metal to the scaffold, wherein the scaffold comprises a biological scaffold and the metal comprises a metal atom or ion.

AC: The method according to any of paragraphs W-AB, wherein the target includes a microbe and the scaffold comprises an antibody against epitopes present on a surface of the microbe.

AD: The method according to any of paragraphs W-AC, wherein the target includes a biological toxin and the scaffold comprises an antibody against the biological toxin.

AE: The method according to any of paragraphs W-AD, further comprising determining presence of the metal in the sample based at least in part on at least a non-fluorescence portion of the optical-spectrum signal.

AF: The method according to any of paragraphs W-AE, further comprising determining presence of the metal in the sample based at least in part on a portion of the optical-spectrum signal extending over a spectral range wider than at least one of 50 nm, 100 nm, 150 nm, 200 nm, or 250 nm.

AG: The method according to any of paragraphs W-AF, wherein the metal is not a heavy metal.

AH: The method according to any of paragraphs W-AG, wherein the metal is not toxic to humans.

AI: An apparatus for detecting a biological target in a sample, the apparatus comprising: a preparation subsystem configured to add a recognition construct to the sample, the recognition construct comprising a metal; a washing subsystem configured to form a washed sample by washing at least some unbound recognition construct out of the sample; a heating subsystem configured to heat at least some of the washed sample; and a spectroscopic detector configured to detect at least some electromagnetic radiation emitted by metal in the at least some of the washed sample in response to the heating of the washed sample.

AJ: The apparatus according to paragraph AI, wherein the heating subsystem comprises a laser.

AK: The apparatus according to paragraph AI or AJ, wherein the heating subsystem comprises two electrodes and a high-voltage power supply connected to the two electrodes and configured to selectively produce a spark across the two electrodes.

AL: The apparatus according to any of paragraphs AI-AK, further comprising a processor and a processor-accessible memory, e.g., at least one computer storage medium, storing instructions executable by the processor to cause the processor to perform operations.

AM: The apparatus according to paragraph AL, the operations comprising determining presence of the metal in the sample based at least in part on at least a non-fluorescence portion of the optical-spectrum signal.

AN: The apparatus according to paragraph AL or AM, the operations comprising determining presence of the metal in the sample based at least in part on a portion of the optical-spectrum signal extending over a spectral range wider than at least one of 50 nm, 100 nm, 150 nm, 200 nm, or 250 nm.

AO: The apparatus according to any of paragraphs AI-AN, wherein the metal is not a heavy metal.

AP: The method according to any of paragraphs AI-AO, wherein the metal is not toxic to humans.

AQ: A computer-readable medium, e.g., at least one computer storage medium, having thereon computer-executable instructions, the computer-executable instructions upon execution configuring a computer to perform operations as any of paragraphs W-AH recites.

AR: A device comprising: a processor; and a computer-readable medium, e.g., at least one computer storage medium, having thereon computer-executable instructions, the computer-executable instructions upon execution by the processor configuring the device to perform operations as any of paragraphs W-AH recites.

AS: A system comprising: means for processing; and means for storing having thereon computer-executable instructions, the computer-executable instructions including means to configure the system to carry out a method as any of paragraphs W-AH recites.

CONCLUSION

Various examples herein permit at least tagging mAbs with metals without loss of mAb function, effectively distinguishing between tagged substances, distinguishing between at least four different targets in the same sample, or aligning spectra using the spectral signature of the substrate.

Steps of various methods described herein can be performed in any order except when otherwise specified, or when data from an earlier step is used in a later step. Example method(s) described herein are not limited to being carried out by components particularly identified in discussions of those methods.

In view of the foregoing, various aspects provide measurement of constituents of a sample. A technical effect of various aspects is to ablate a small quantity of the sample to form a plasma and to measure the constituents of the plasma spectroscopically. A technical effect of various aspects is to provide a metal-labeled target. A further technical effect of various aspects is to present a visual representation of the detected spectra or corresponding abundances of selected biomolecules on an electronic display. This can permit medical or scientific personnel to more readily determine whether a sample contains a target of interest, e.g., at a selected concentration or quantity.

The invention is inclusive of combinations of the aspects described herein. References to "a particular aspect" (or "embodiment" or "version") and the like refer to features that are present in at least one aspect of the invention. Separate references to "an aspect" (or "embodiment") or "particular aspects" or the like do not necessarily refer to the same aspect or aspects; however, such aspects are not mutually exclusive, unless otherwise explicitly noted. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected within the spirit and scope of the invention.

The invention claimed is:

1. A system for characterizing a target within a sample, the system comprising:
   a substrate configured to retain the sample, the substrate comprising a silicon surface and a capture antibody coupled to the silicon surface, the capture antibody being configured to attach to the target;
   the sample comprising a biomolecular recognition construct, wherein the biomolecular recognition construct comprises:
      a scaffold configured to couple with the target;
      a polymer coupled to the scaffold and comprising a metal-chelating ligand; and
      a first metal atom or ion linked to the metal-chelating ligand;
   an energy source configured to transform the first metal atom or ion in the sample into a plasma;
   an optical spectroscopic detector configured to detect electromagnetic radiation emitted by the plasma and to provide an optical-spectrum signal of the sample based at least in part on at least some of the electromagnetic radiation;
   a processor; and
   a memory storing instructions executable by the processor to cause the processor to perform operations comprising:
      generating a normalized optical-spectrum signal by normalizing the optical-spectrum signal of the sample with respect to an optical-spectrum signal of a material of the substrate; and
      determining presence of the first metal atom or ion in the sample based at least in part on the normalized optical-spectrum signal.

2. The system according to claim 1, the operations further comprising:
   performing spectral unmixing on the optical-spectrum signal of the sample;
   performing constrained energy minimization on the optical-spectrum signal of the sample; or
   determining presence of the metal atom or ion in the sample by applying the optical-spectrum signal of the sample to a multi-class classifier selected from the group consisting of a support vector machine, a kernel estimator, a nearest-neighbor classifier, a decision tree, a decision forest, a neural network, or a deep neural network.

3. The system according to claim 1, the operations further comprising:
   determining presence of a second metal atom or ion in the sample based at least in part on the optical-spectrum signal of the sample, wherein:
      the first metal atom or ion is an atom or ion of a first element; and
      the second metal atom or ion is an atom or ion of a second element different from the first element.

4. The system according to claim 1, wherein the substrate comprises a silicon wafer.

5. The system according to claim 1, wherein the substrate comprises recognition macromolecules that comprise the capture antibody.

6. The system according to claim 1, wherein the scaffold comprises at least one of: adNectin, iMab, anticalin, designed ankyrin repeat protein (DARPin), affilin, tetranectin, or avimer.

7. The system according to claim 1, wherein the biomolecular recognition construct consists essentially of:
   the scaffold;
   the polymer; and
   the first metal atom or ion bound to the metal-chelating ligand.

8. The system according to claim 7, wherein the scaffold consists essentially of a structure selected from the group consisting of adNectin, iMab, anticalin, designed ankyrin repeat protein (DARPin), affilin, tetranectin, and avimer.

9. The system according to claim 1, wherein the biomolecular recognition construct comprises:
   at least one scaffold, the at least one scaffold comprising the scaffold;
   one or more polymers, the one or more polymers comprising the polymer; and
   one or more metal atoms or ions, each of the one or more metal atoms or ions bound to a respective metal-chelating ligand of a corresponding polymer of the one or more polymers, wherein the one or more metal atoms or ions comprise the first metal atom or ion, and the metal-chelating ligand is one of the respective metal-chelating ligands.

10. The system according to claim 9, wherein the scaffold consists of a structure selected from the group consisting of adNectin, iMab, anticalin, designed ankyrin repeat protein (DARPin), affilin, tetranectin, and avimer.

11. The system according to claim 1, wherein the metal-chelating ligand comprises diethyl enetriaminepenta-acetic acid (DTPA),
   wherein the first metal atom or ion linked to the metal-chelating ligand comprises a lanthanide.

12. The system according to claim 1, wherein the capture antibody is an antitoxin antibody.

13. The system according to claim 1, wherein generating the normalized optical-spectrum signal comprises normalizing the optical-spectrum signal of the sample with respect to an optical-spectrum signal of silicon.

* * * * *